US009861728B2

(12) United States Patent
Farnan et al.

(10) Patent No.: US 9,861,728 B2
(45) Date of Patent: Jan. 9, 2018

(54) HEART ASSIST SYSTEM AND METHODS

(71) Applicant: CircuLite, Inc., Teaneck, NJ (US)

(72) Inventors: Robert C. Farnan, Fort Lauderdale, FL (US); Robert G. Hudgins, Monticello, MN (US); John Dockter, Eden Prairie, MN (US)

(73) Assignee: CircuLite, Inc., Teaneck, NJ (US)

( * ) Notice: Subject to any disclaimer, the term of this patent is extended or adjusted under 35 U.S.C. 154(b) by 420 days.

(21) Appl. No.: 14/715,794

(22) Filed: May 19, 2015

(65) Prior Publication Data
US 2015/0335801 A1 Nov. 26, 2015

Related U.S. Application Data

(60) Provisional application No. 62/000,788, filed on May 20, 2014.

(51) Int. Cl.
A61M 5/00 (2006.01)
A61M 1/10 (2006.01)
A61M 1/12 (2006.01)

(52) U.S. Cl.
CPC ........... *A61M 1/1008* (2014.02); *A61M 1/101* (2013.01); *A61M 1/122* (2014.02)

(58) Field of Classification Search
CPC .... A61M 1/1008; A61M 1/122; A61M 1/101; A61M 1/3653
See application file for complete search history.

(56) References Cited

U.S. PATENT DOCUMENTS

| 8,343,029 | B2 | 1/2013 | Farnan et al. |
|---|---|---|---|
| 8,821,366 | B2 | 9/2014 | Farnan et al. |
| 8,821,527 | B2 | 9/2014 | Farnan et al. |
| 2002/0128587 | A1 | 9/2002 | Aboul-Hosn et al. |
| 2007/0135686 | A1 | 6/2007 | Pruitt et al. |

(Continued)

FOREIGN PATENT DOCUMENTS

WO 2014202051 A1 12/2014

OTHER PUBLICATIONS

European Patent Office, International Search Report and Written Opinion in PCT Application Serial No. PCT/US2015/031500, dated Feb. 16, 2016.

(Continued)

*Primary Examiner* — Philip R Wiest
(74) *Attorney, Agent, or Firm* — Christopher & Weisberg, P.A.

(57) ABSTRACT

A system for drawing blood from a heart of a patient, includes a blood pump, an outflow cannula and a flexible cannula assembly. The cannula assembly further includes a flexible cannula body including a proximal end, a distal end, an inner wall defining a lumen, and an outer wall. A tip is coupled with the distal end of the cannula body, and an anchor is coupled to the tip. The anchor is configured to engage an internal structure of the heart and resists movement of the cannula assembly in at least one direction along the flexible cannula body. A ring member is configured to be coupled to the heart wall and is positioned at least partially around the outer wall of the cannula body proximally relative to the tip. The ring member is further configured to provide hemostasis between the heart wall and the cannula body.

50 Claims, 29 Drawing Sheets

(56) References Cited

U.S. PATENT DOCUMENTS

| | | |
|---|---|---|
| 2008/0021552 A1 | 1/2008 | Gabbay |
| 2008/0076959 A1 | 3/2008 | Farnan et al. |
| 2009/0112050 A1* | 4/2009 | Farnan ................ A61M 1/3653 600/16 |
| 2012/0059213 A1 | 3/2012 | Spence |
| 2012/0130391 A1 | 5/2012 | Sundt, III et al. |
| 2014/0107399 A1 | 4/2014 | Spence |
| 2014/0257018 A1 | 9/2014 | Farnan |
| 2014/0303427 A1 | 10/2014 | Kerkhoffs et al. |
| 2015/0005570 A1 | 1/2015 | Fritz et al. |

OTHER PUBLICATIONS

The International Bureau of WIPO, International Preliminary Report on Patentability in PCT Application Serial No. PCT/US2015/031500, dated Dec. 1, 2016.

European Patent Office, Invitation to Pay Additional Fees in PCT Application No. PCT/US15/031500, dated Aug. 28, 2015.

* cited by examiner

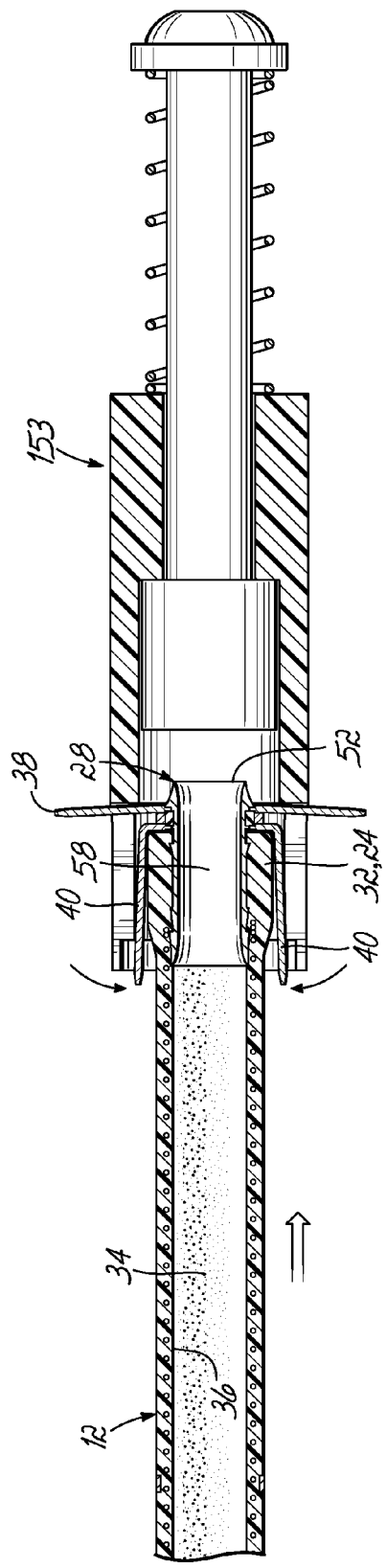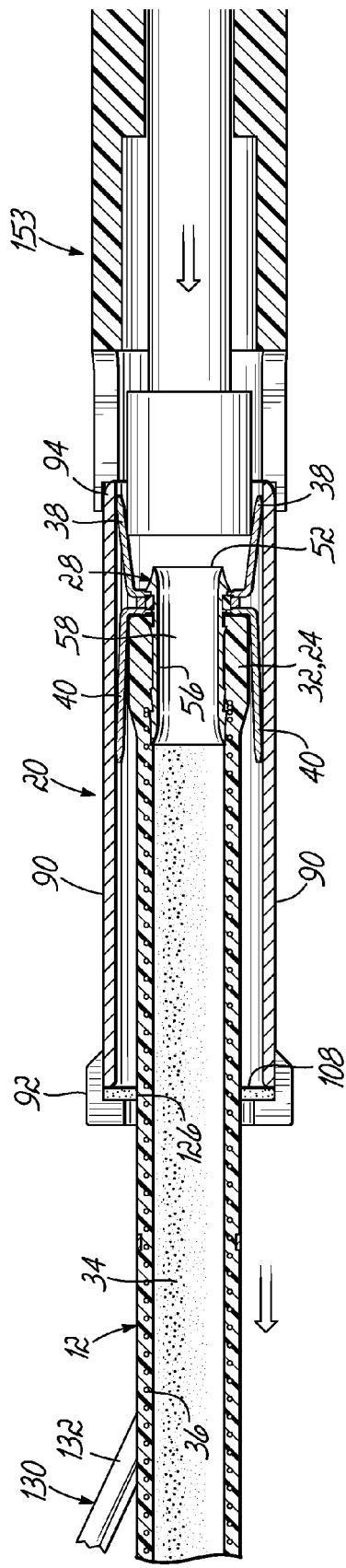

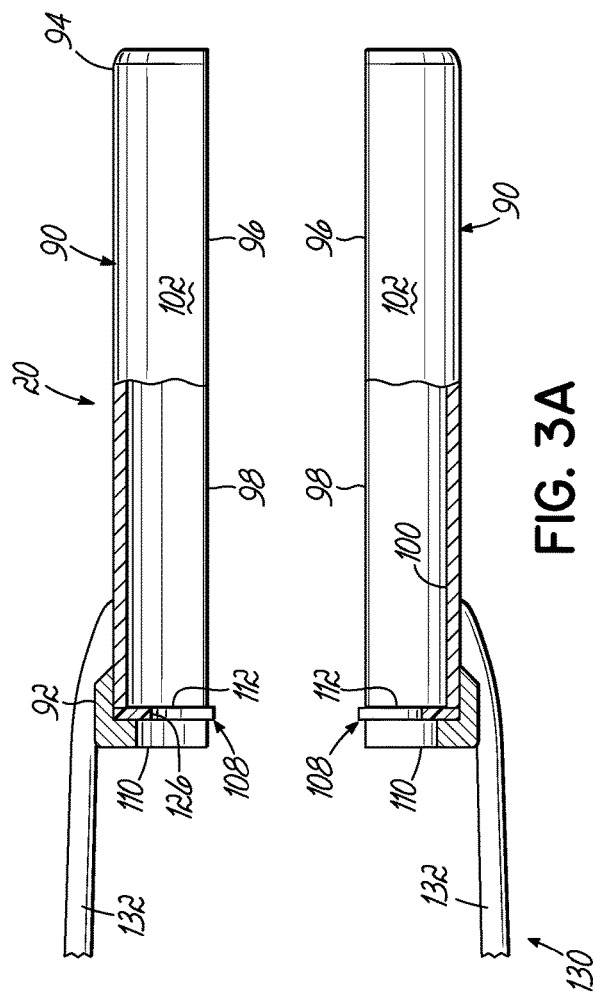
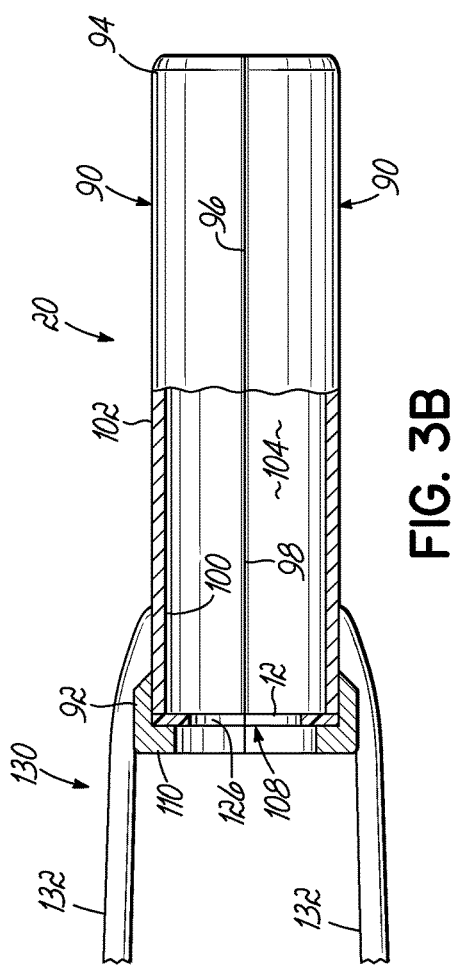
FIG. 3A
FIG. 3B

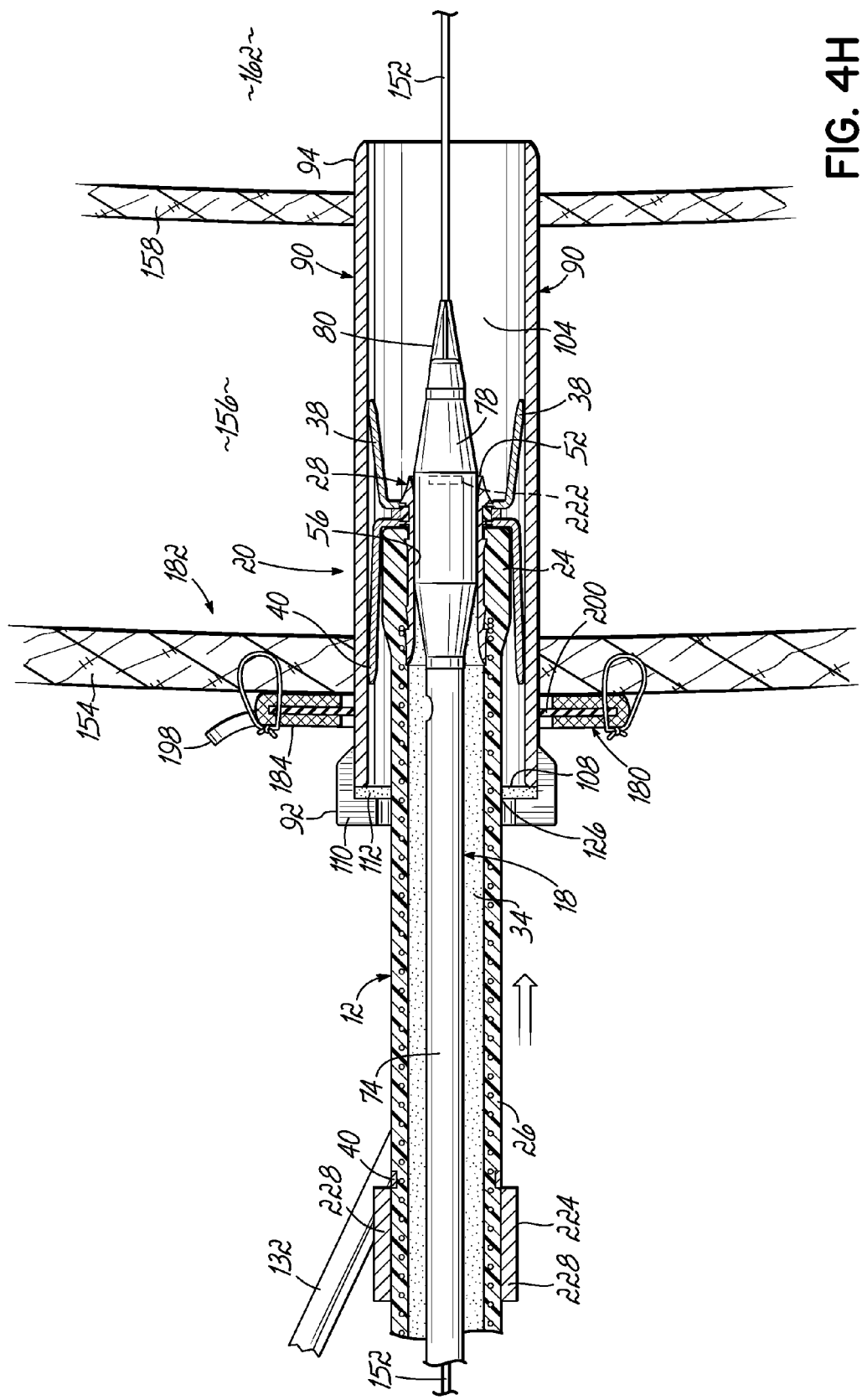

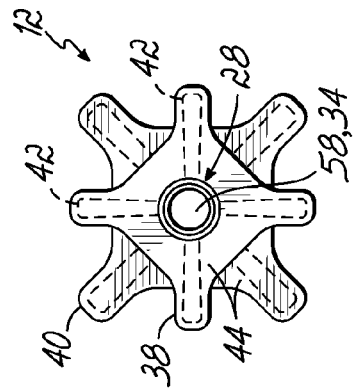
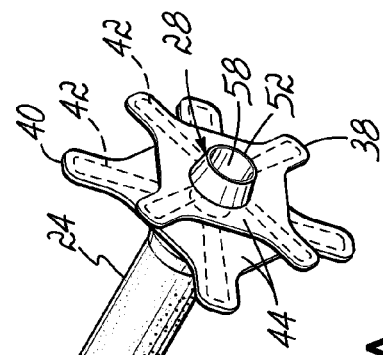
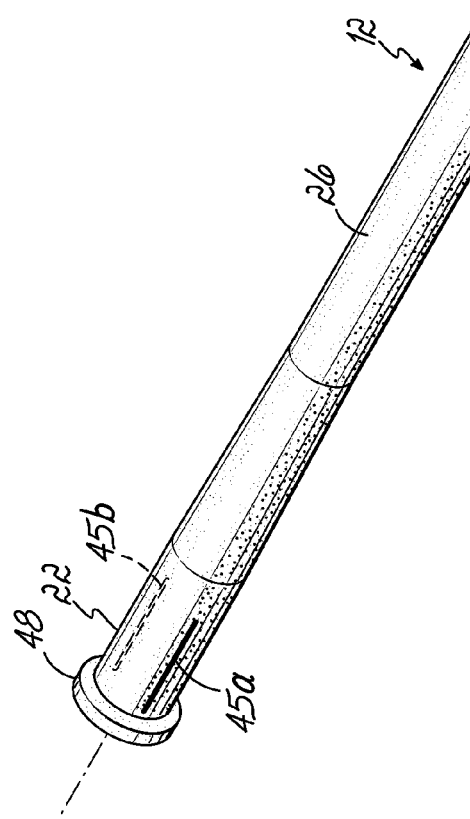
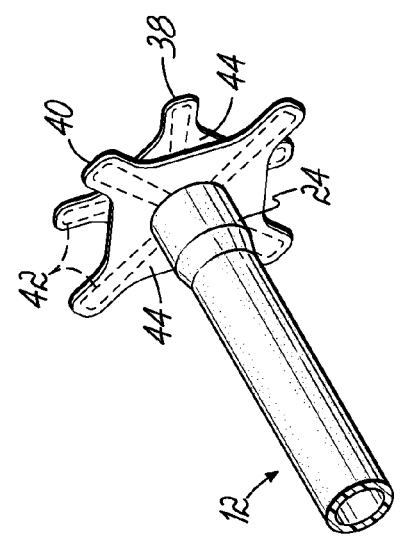
FIG. 5C
FIG. 5A
FIG. 5B

HEART ASSIST SYSTEM AND METHODS

CROSS-REFERENCE TO RELATED APPLICATION

This application claims the priority of Application Ser. No. 62/000,788 filed May 20, 2014, the disclosure of which is hereby incorporated by reference herein.

TECHNICAL FIELD

The present invention generally relates to systems and methods for assisting with pumping blood from the heart of a patient and improving blood circulation.

BACKGROUND

The human heart is the muscle that is responsible for pumping blood throughout the vascular network. Veins are vessels that carry blood toward the heart while arteries carry blood away from the heart. The human heart consists of two atrial chambers and two ventricular chambers. Atrial chambers receive blood from the body and the ventricular chambers, which include larger muscular walls, pump blood from the heart. A septum separates the left and the right sides of the heart. Movement of the blood is as follows: blood enters the right atrium from either the superior or inferior vena cava and moves into the right ventricle. From the right ventricle, blood is pumped to the lungs via pulmonary arteries to become oxygenated. Once the blood has been oxygenated, the blood returns to the heart by entering the left atrium, via the pulmonary veins, and into the left ventricle. Finally, the blood is pumped from the left ventricle into the aorta and the vascular network.

For the vast majority of the population, the events associated with the movement of blood happen without circumstance. However, for many people the heart fails to provide adequate pumping capabilities. These heart failures may include congestive heart failure (commonly referred to as heart disease), which is a condition that results in any structural or functional cardiac disorder that impairs the ability of the heart to fill with or pump blood throughout the body. Presently, there is no known cure for heart disease and long-term treatment is limited to a heart transplant. With only a little over 2,000 patients receiving a heart transplant each year, and over 16,600 more on the waiting list for a heart, there is a persisting need for a cure or at the minimum a means of improving the quality of life of those patients on the waiting list.

One such means of bridging the time gap while awaiting a transplant is a circulatory assist system. These systems, originally developed over a decade ago, provide assistance to the heart by way of a mechanical pump. In this way, blood is circulated throughout the vascular network despite the diseased heart tissue. Traditionally, these circulatory assist systems include an implantable or extracorporeal pump, a controller (internal or external), and inflow and outflow tubes connecting the pump to the vascular network. FDA approved circulatory assist systems partially relieve symptoms of breathlessness and fatigue associated with severe heart failure and drastically improve quality of life.

However, the surgical process associated with the circulatory assist system is highly invasive. At the very least the procedure involves a thoracotomy, i.e., the opening of the thoracic cavity between successive ribs to expose the internal organs. More typical is cardiac surgery, generally known as open-heart surgery, where the sternum is cut and split to expose the internal organs. Once the thoracic cavity is accessed, the surgeon must enter the thoracic space and puncture both the pericardium and the myocardial wall. There are great risks and an extensive recovery time associated with the invasive nature of the implantation surgery. As such, some patients with severe symptoms are not healthy enough for surgery to receive a circulatory assist system.

DETAILED DESCRIPTION OF DRAWINGS

FIGS. 2B through 2E show a side cross-sectional view various steps of assembling the delivery system of FIG. 2A configured to be directed to the heart.

FIG. 3A is a top view showing the jaws of the delivery sheath of FIG. 2A in an open configuration.

FIG. 3B is a view similar to FIG. 3A showing the jaws of the delivery sheath in a closed configuration.

FIGS. 4B through 4N are side elevational views in partial cross-section of an exemplary method of securing a flexible cannula assembly to a heart of a patient for directing blood from the heart.

FIG. 5A is a perspective view of the flexible cannula assembly shown in FIG. 2A.

FIG. 5B is a rear perspective view of the flexible cannula assembly of FIG. 2A, showing details of the distal end thereof.

FIG. 5C is an end view of the flexible cannula assembly shown in FIG. 5A.

DETAIL DESCRIPTION

Figure 1:
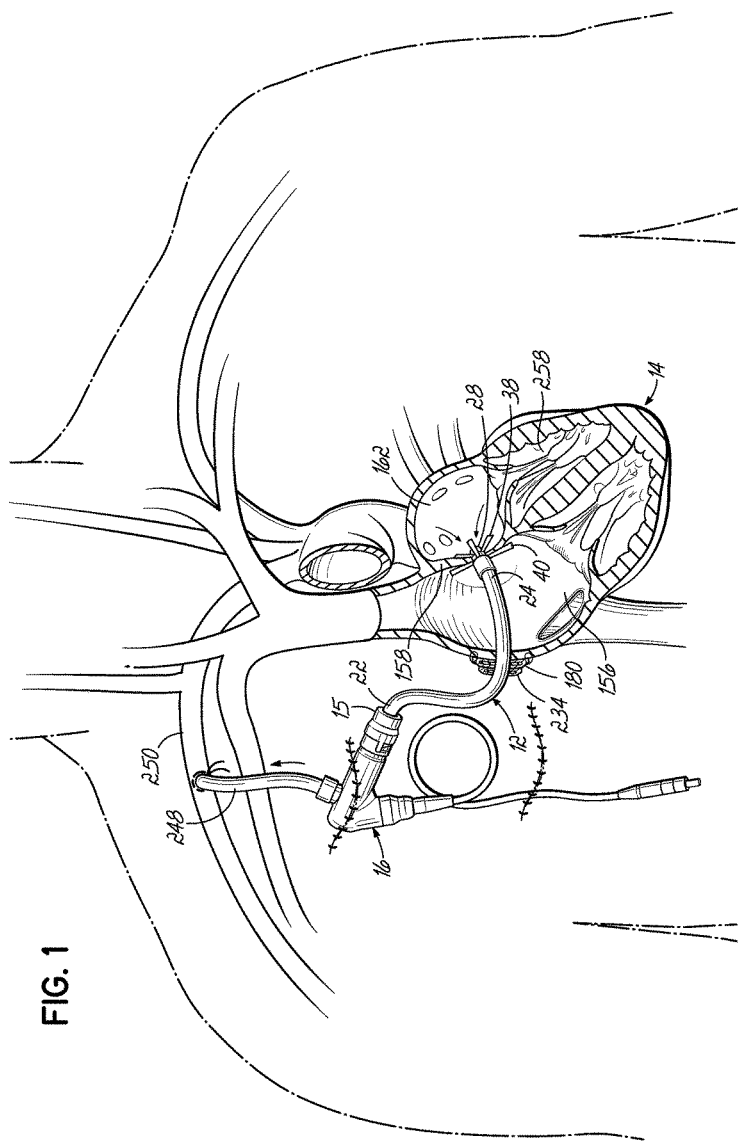
FIG. 1 is a diagrammatic view of a patient with the heart in cross section and a system of one illustrative first embodiment of the invention implanted in the patient.

Referring now to FIGS. 1, 2A-2E and 3A-3C, components of a delivery system 10, for delivering a flexible cannula assembly 12 to a heart 14 of a patient, are shown. Once the cannula assembly 12 is delivered to the heart 14, such that one end of the cannula assembly 12 is in fluid communication with a chamber of the heart 14, for example, the other end of the cannula assembly 12 is fluidly communicated to an inlet 15 of a pump 16. Thus, operating the pump 16 causes blood to be drawn from the heart 14, through the cannula assembly 12, and into the patient circulatory system.

The delivery system 10 includes a balloon catheter 18, the flexible cannula assembly 12, and a delivery sheath 20. The flexible cannula assembly 12 includes a proximal portion 22 and a distal portion 24. The flexible cannula assembly 12 includes a flexible cannula body 26, and a tip 28. The cannula body 26 includes a proximal end 30 and a distal end 32. The cannula body 26 also includes lumen 34 defined by an inner wall 36 and extending between the proximal and distal ends 30, 32. Also referring to FIGS. 5A and 5B, the cannula assembly 12 includes the tip 28, which is coupled to the distal end 32 of the cannula body 26, and first and second anchors 38, 40 coupled to the tip 28. Each anchor is comprised of a plurality of struts 42 (shown in hidden lines). As illustrated, each of the first and second anchors 38, 40 includes a porous polymeric structure 44 over the struts 42. The first anchor 38 is positioned distally relative to the second anchor 40, and includes a smaller cross-sectional area than the second anchor 40. In one embodiment, the complete cannula assembly 12, once properly implanted, will create a shunt for oxygenated blood to flow from the left atrium of the heart 14 to an implantable pump 16, and the vascular network beyond.

In one embodiment, the cannula body 26 may be malleable, similar to the cannula disclosed in U.S. patent application Ser. No. 13/788,039, entitled MALLEABLE CANNULA, assigned to the assignee of the present invention, and incorporated herein by reference, in its entirety. Referring to FIGS. 5A-5B, the cannula body 26, at or near the proximal end 30, includes a solid line 45a and a diametrically opposed dashed line 45b. The lines are provided in order to provide a visual communication of the relative rotational positions between the proximal end 30 of the cannula body 26 and the pump 16. The proximal end 30 of the cannula body 26 also includes a lip 48. The cannula assembly 12 may be coupled to the pump 16 in the same or similar manner as described in U.S. Provisional Patent Application Ser. No. 61/809,984, entitled BLOOD FLOW SYSTEM WITH OPERATOR ATTACHABLE COMPONENTS, assigned to the assignee of the present invention, and incorporated herein by reference.

Figure 2A:
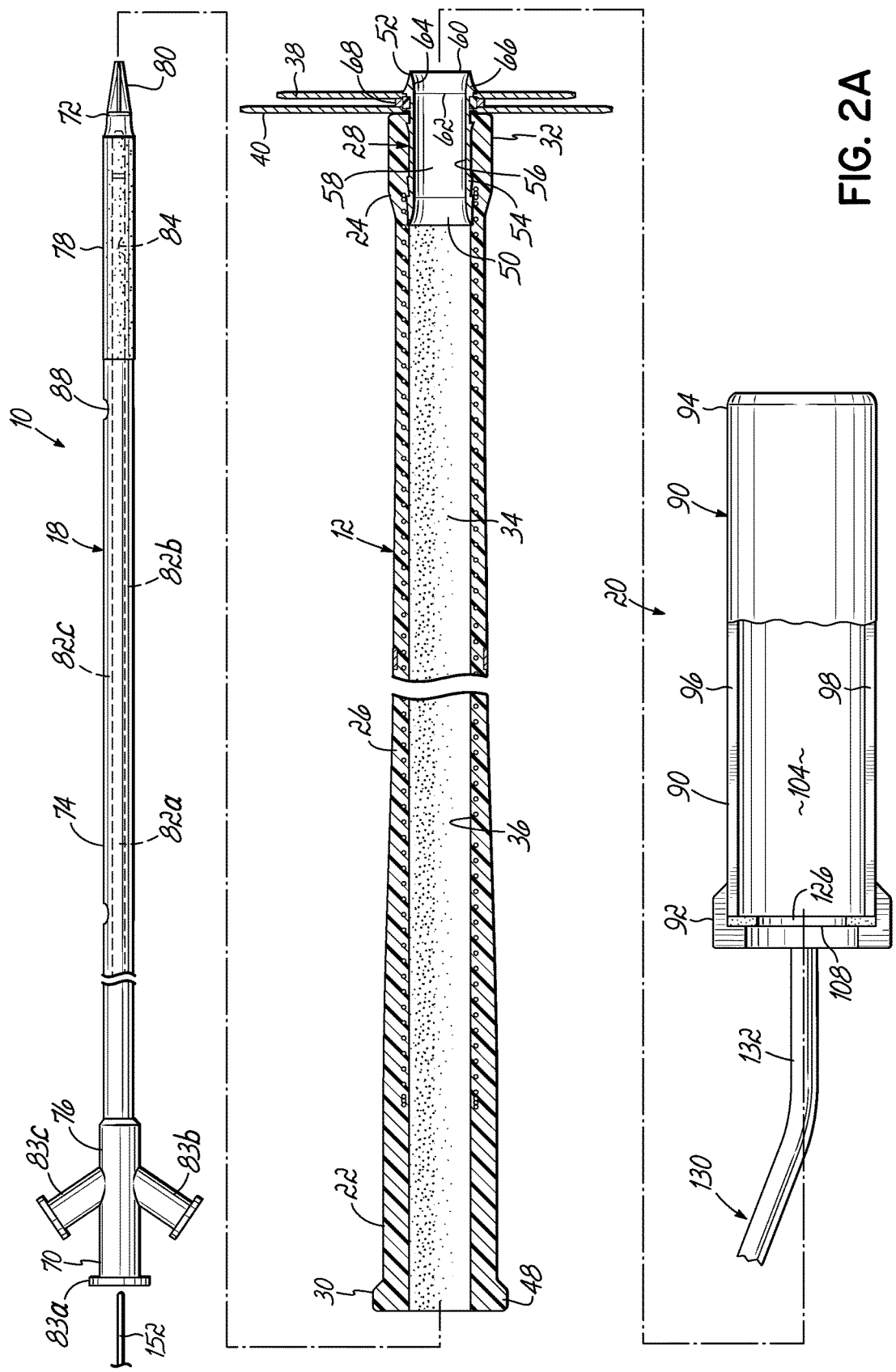
FIG. 2A shows side and cross sectional views of several components of a delivery system and a cannula assembly according to the first embodiment.

Still referring to FIG. 2A, it may be advantageous to provide the tip 28 of the cannula assembly 12 with characteristics that improve blood flow characteristics of the cannula assembly 12. Therefore, the tip 28 may include characteristics similar to those disclosed in U.S. Pat. No. 8,343,029, entitled TRANSSEPTAL CANNULA, TIP, DELIVERY SYSTEM, AND METHOD, and U.S. Patent Application Publication No. 2013/0172661, also entitled TRANSSEPTAL CANNULA, TIP, DELIVERY SYSTEM, AND METHOD, both assigned to the assignee of the present invention and incorporated herein by reference. In that regard, tip 28 includes a proximal portion 50, a distal portion 52, and a body 54 extending the length of the tip 28. Tip 28 includes an inner wall 56 defining a lumen 58, which includes certain dimensions that provide advantageous fluid flow. The distal portion 52 of tip 28 includes first and second ends 60, 62 having first and second inner diameters respectively. The second end 62 is more proximal than the first end 60 and the first inner diameter is larger than the second inner diameter. In one embodiment of the tip 28, the difference in the first and second inner diameters defines at least a portion of the tip 28 as a generally campanulate, or bell-shaped, member. In between the first and second ends of the distal portion 52 is a generally curvilinear portion 64, thereby defining at least a portion of the tip 28 as a generally campanulate shape. As shown, the proximal portion 50 of the tip 28 also includes a similarly shaped campanulate portion.

The campanulate shaped portions of the tip 28 provide fluid flow benefits for the circulatory assist system. More specifically, the campanulate shape provides a smoother flow transition, and thus lower pressure losses, as a fluid is moving from the larger heart chamber, into the relatively smaller of lumen 34 of the cannula body 26. Reducing pressure losses of the fluid or blood entering the tip 28 provides for a more advantageous circulatory assist system. Furthermore, advantageously, the campanulate shape reduces the occurrence of turbulence of blood at the tip 28 and in the cannula when blood is drawn into the lumen 34, thereby increasing the overall efficiency and efficacy of the system.

The generally campanulate tip 28 may be free of imperfections that may cause thrombus formation. For example, the tip 28 may be polished in order to remove any imperfections that may lead to thrombus formation. Moreover, the transition between the cannula body 26 and the tip 28 may be smooth and free of irregularities that may cause thrombus.

The tip 28 may further include one or more barbs 66 on the body of the tip 28. Barbs 66 provide resistance against the undesired removal of the cannula body 26 from the tip 28. The tip 28 includes a ring 68, provided for potentially several reasons. For example, the ring 68 may act in a manner as to engage the anchors 38, 40. Advantageously, the ring 68 may be provided with a porous polymer structure (not shown) such as polyester fabric wherein tissue from the septum may grow and embed within the porous polymeric structure to provide greater structural stability. The distal end 32 of cannula body 26 may essentially abut one of the anchors 38, 40. Further, additional rings 68 may be included and could be used to seat the anchors 38, 40 and can be keyed in a way so as to maintain an orientation of the anchors 38, 40.

In one embodiment, the tip body 54 is constructed from titanium alloy, such as TiAl 6Va EL 1, by standard turning, wire electrical discharge machining (EDM), or other machining processes. In this regard, and as shown most clearly in the cross-sectional view of FIG. 1A, the tip 28 is a rigid tip 28 of unitary construction.

Still referring to FIG. 2A, the balloon catheter 18 is illustrated for use as a part of the delivery system 10 for directing the cannula assembly 12 to the heart 14. The balloon catheter 18 includes a proximal portion 70, a distal portion 72, and a shaft 74 therebetween. The proximal portion 70 includes a 3-way hub 76, and the distal portion 72 includes a balloon 78 and an obturator tip 80. The 3-way hub 76 communicates with three lumens 82a, 82b, 82c (FIG. 2E) within the shaft 74, respectively, to allow for guidewire passage, balloon inflation, and flushing of the system 10. More particularly, a first lumen 82a extends between the first port 83a of the hub 76 and the distal portion 72, and is configured to receive and allow passage of the guidewire 152. A second lumen 82b, used for inflating the balloon 78, extends from the second port 83b of the hub 76 to an outlet 84 in communication with an interior cavity 86 (FIG. 2E) of the balloon 78. A third lumen 82c, used for flushing the system 10, extends from the third port 83c of the hub 76 to a side outlet 88 (FIGS. 2D and 2E) along the shaft 74. The distal portion 72 of the balloon catheter 18 includes the obturator tip 80 for separating and creating an opening in the tissue through which the system 10 may be inserted. The first lumen for the guidewire 152 extends from the proximal portion 70 to the distal portion 72 of the balloon catheter such that part of the lumen extends through the obturator tip 80.

Figure 7A:
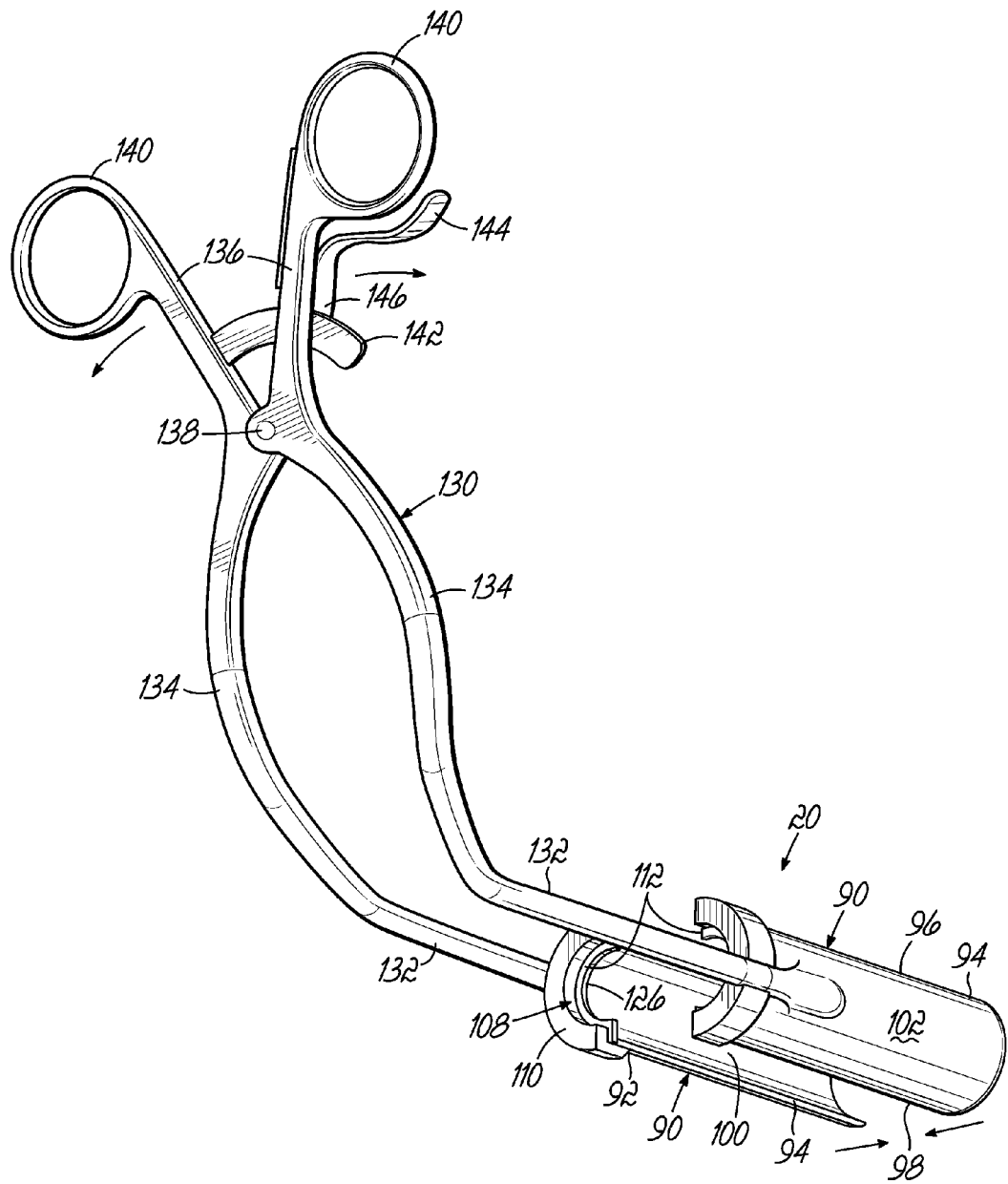
FIG. 7A is a rear perspective view of one embodiment of the delivery sheath, showing the jaws of the delivery sheath in the open configuration.
Figure 7B:
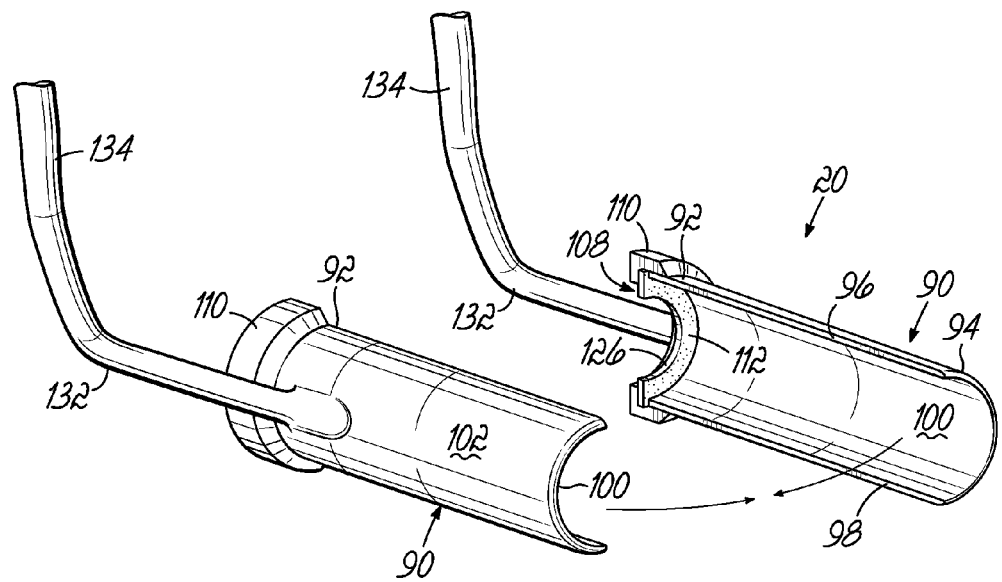
FIG. 7B is a detailed front perspective view of the delivery sheath of FIG. 7A, showing the jaws of the delivery sheath in the open configuration.
Figure 7C:
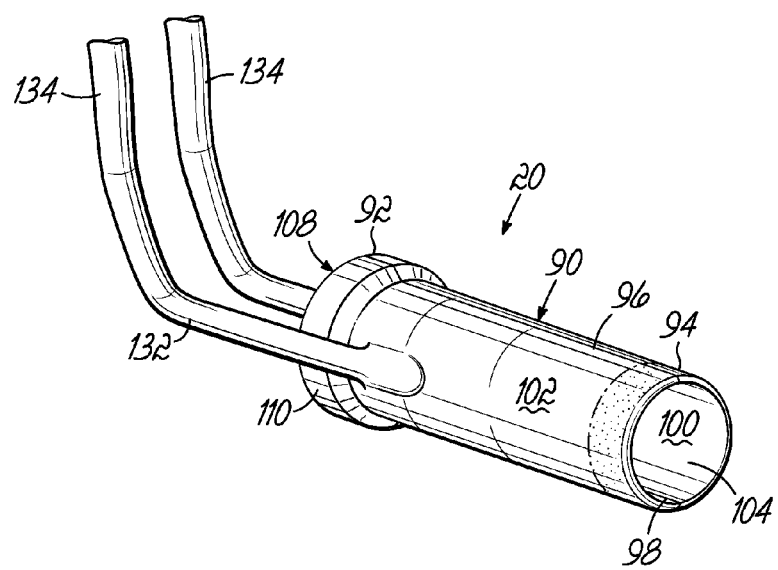
FIG. 7C is a view similar to FIG. 7B, showing the jaws of the delivery sheath in the closed configuration.

Referring additionally to FIGS. 7A-7C, the delivery sheath 20 includes a set of rigid jaws 90 movable between an open configuration (FIGS. 3A, 7A-7B) and a closed configuration (FIGS. 2B-2E, 3B, 7C). Each of the jaws 90 includes a generally semi-annular shape in cross-section and extends between a proximal portion 92 and a distal portion 94. Each of the jaws 90 also includes a first medial edge 96 and a second medial edge 98. The jaws 90 also include inner and outer walls 100, 102 that extend between the proximal and distal portions 92, 94. The inner and outer walls 100, 102 of each jaw 90 also extend between the first and second medial edges 96, 98. When the jaws 90 are in the closed configuration, the first medial edges 96 of each jaw 90 abut one another, while the second medial edges 98 of each jaw 90 abut one another. Thus, in the closed configuration, the jaws 90 define a lumen 104 extending between the proximal and distal portions 92, 94. Furthermore, in the closed configuration, each of the jaws 90 extends parallel to a central axis of the lumen 104 (in the proximal and distal directions). As shown, due to the shape of the inner walls 100 of each of the jaws 90, the lumen 104 is generally circular in cross-section. Of course, the shape of the lumen 104 may change according to a change in shape of the jaws 90. As shown, the delivery sheath 20 includes two jaws 90. However, the delivery sheath 20 may include more than two jaws 90 that include similar features as described herein with respect to the embodiment having two jaws 90.

As will be described in more detail below, the delivery sheath 20 may require sealing at or near the proximal portion 92 when a portion of the cannula assembly 12 is directed into, and received by, the delivery sheath 20. In that regard, delivery sheath 20 includes a sealing member 108, essentially half of which is coupled to each jaw 90. The sealing member 108 includes a radially outward seal housing 110 and a radially inward seal 112.

When the jaws 90 are in the closed configuration, the parts of the seal housing 110 remain spaced from one another. However, when the jaws 90 are in the closed configuration, each part of the seal 112 generally abuts the other. The seal 112 may comprise a polymeric or rubber-like material such as silicone, urethane, etc., that include pliability and resiliency features to provide for sealing when the cannula assembly 12 is directed into the delivery sheath 20. Further to that end, the cross-sectional dimension, such as diameter, of the aperture 126 must be sized to be in an interference fit with at least a portion of the cannula body 26. Preferably, the amount of interference fit between the seal 112 and cannula body 26 cause at least slight compression of the seal 112 when the delivery sheath 20 in the closed configuration receives the flexible cannula assembly 12. The spaced apart configuration of the seal housing 110 in the closed configuration provides an amount of tolerance that allows the compression of the seal 112 as just described.

It may also be advantageous to provide a seal (not shown) at the first and second medial edges 96, 98 to prevent fluids from leaking out of the lumen 104 when being flushed, as described herein below. The elongated sealing portion may comprise a polymeric or rubber-like material such as silicone, urethane, etc., that include pliability and resiliency features to provide for sealing when the elongated sealing portions abut one another. When the jaws 90 are in the closed configuration, the elongate sealing portions (not shown) may be at least slightly compressed when abutting one another to enhance the sealing properties.

The delivery sheath 20 also includes a set of hingedly coupled handle members 130 that are operable to move the jaws 90 relative to one another, and between the open and closed configurations. Each of the handle members 130 includes a distal portion 132 coupled to the proximal portion of a respective jaw 90. As shown, each distal portion 132 extends generally parallel to the axis along which the jaws 90 extend, such that the distal portions 132 extend generally parallel to the central axis of the lumen 104, when the jaws 90 are in the closed configuration. Each handle member 130 includes an intermediate portion 134 and a proximal portion 136 that each extend at an obtuse angle relative to the distal portion 132. The angled configuration allows for direct visualization through the mini-thoracotomy incision of the thoracic cavity, heart 14, and other structures as the delivery system 10 is being directed into the heart 14. The intermediate portions 134 are essentially defined as arms, and extend to a pivot 138 that allows each of the jaws 90 to pivot relative to one another. The proximal portions 136 include finger holes 140 that allow for insertion of a clinician's thumb and finger (e.g.), respectively, therefore allowing the clinician to move the jaws 90 relative to one another.

The proximal portion 136 also includes a locking mechanism 142 that is operably coupled to the handle members 130. The locking mechanism 142 may be moved between a first locking state whereby the jaws 90 may move relative to one another (i.e., unlocked), and a second locking state, whereby the locking mechanism 142 resists or prevents movement of the jaws 90 relative to one another (i.e., locked). The locking mechanism 142 is configured such that it may be in the second locking state (i.e., locked) when the jaws 90 are in the closed configuration, the open configuration, or in a position between the open and closed configurations. Essentially, the locking mechanism 142 can be locked in the open configuration, the closed configuration, and/or any position between the open and closed configurations. The locking mechanism 142 may be moved between the first and second locking states by actuation of resilient lever 144, which interacts with the locking flange 146 extending from one of the handle members 130.

Before the delivery system 10 may be traversed over the guidewire 152, the delivery system 10 is assembled in order to be directed, as a unit, to the heart 14. A loading device 153 is used as more specifically set forth in U.S. Pat. No. 8,821,366, the disclosure of which is hereby fully incorporated herein by reference. Once the delivery system 10 is assembled, it may then be traversed over a guide-element, such as a guidewire 152. Referring to FIGS. 2A-2E and 3A-3C, in order to begin assembly of the delivery system 10, the jaws 90 are moved to the closed configuration and preferably locked in the closed configuration, as described above. Then, the distal portion 24 of the cannula assembly 12, including the distal portion of the cannula body 26, and the tip 28, may be directed into the lumen 104 of the delivery sheath 20.

Figure 2D:
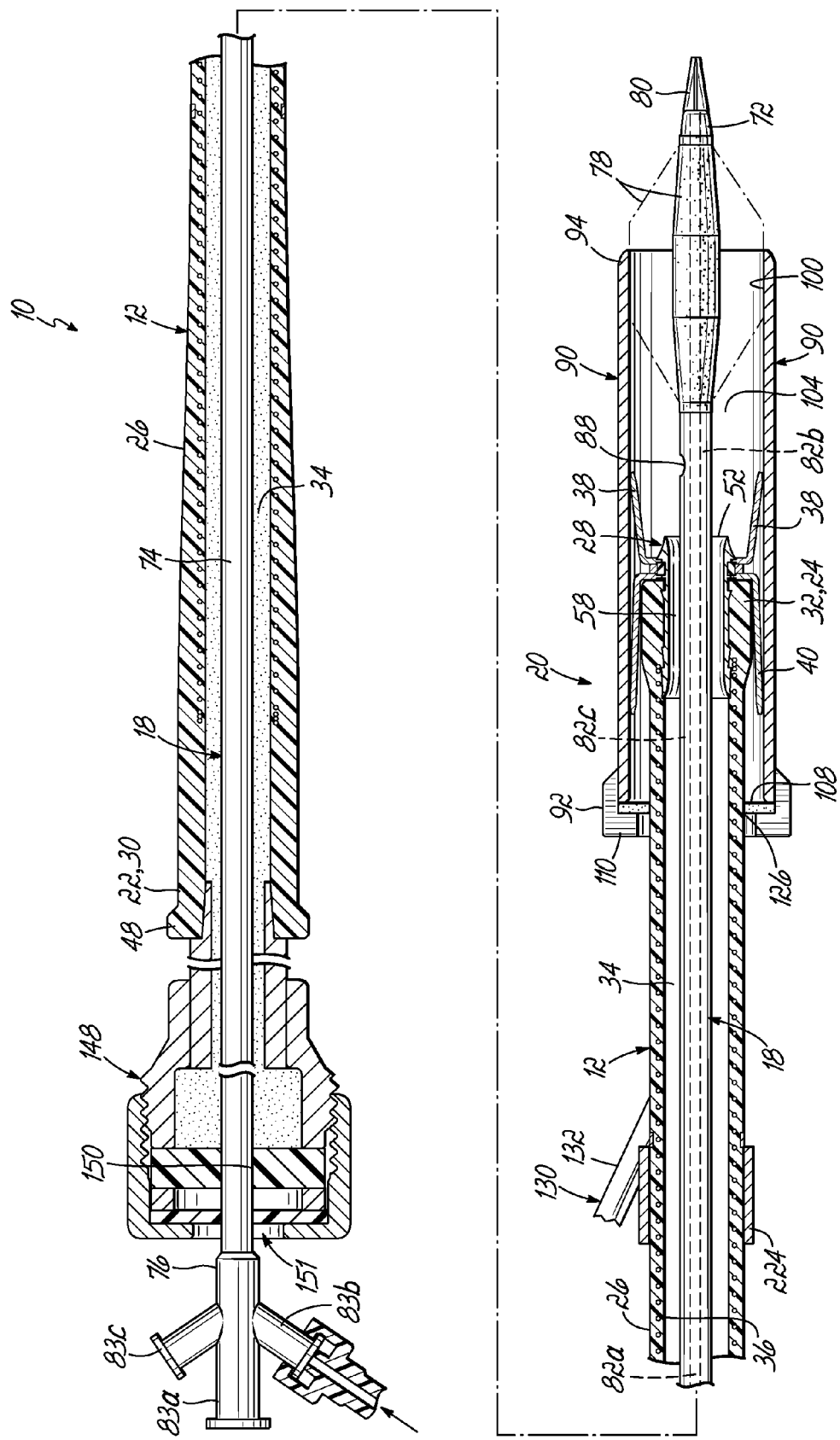

The first and second anchors 38, 40 are folded into the contracted state within the lumen 104 of the delivery sheath 20. In that regard, as shown in FIG. 2B, the cannula assembly 12 is directed into the lumen 104 at the proximal portion 92 of the delivery sheath 20 such that the first and second anchors 38, 40 are folded in a first direction (proximal as shown) to the contracted state. The cannula assembly 12 is directed further in the distal direction towards the distal portion 94 of the delivery sheath 20 until the first anchor 38 exits from the lumen 104, as shown in FIG. 2C. Upon exiting the distal portion 94, the first anchor 38 moves to the expanded state. However, the cannula assembly 12 is moved an amount relative to the delivery sheath 20 such that only the first anchor 38 exits from the lumen 104 and moves to the expanded state. The cannula assembly 12 is then retracted proximally towards the proximal end of the delivery sheath 20 such that the expanded first anchor 38 is folded in the distal direction, as shown in FIG. 2D.

Alternatively, in order to fold the first and second anchors 38, 40 into the contracted states, the delivery sheath 20 may be positioned around the cannula body 26, in the open configuration, at a point proximal of the tip 28 such that the distal portion 94 of the jaws 90 is spaced proximally from the tip 28. Then, the delivery sheath 20 may be moved to the closed configuration whereby the cannula assembly 12 may be moved relative thereto to fold the anchors. More particularly, the cannula assembly 12 may be moved or retracted in the proximal direction, whereby each of the first and second anchors 38, 40 is folded into the contracted state in the distal direction. The cannula assembly 12 may then be further retracted in the second, proximal direction until the second anchor 40 exits from the lumen 104 at the proximal portion 92 and moves to the expanded state. The cannula assembly 12 may then be directed in the distal direction so that the expanded second anchor 40 is folded in the proximal direction.

The distal end of the balloon catheter 18 may then be directed into the proximal portion 30 and through the lumen 34 of the cannula body 26 (before or after the anchors 38, 40 are folded into the delivery sheath 20). As shown, a sealing plug or cap 148 (FIG. 2D) is coupled to the proximal portion 30 of the cannula body 26, for reasons discussed hereinbelow. The sealing plug 148 may be coupled to the proximal portion 30 of the cannula body 26 prior to the balloon catheter 18 being directed therein. The sealing plug 148 includes an aperture 150 that allows the traversal of the shaft 74 of the balloon catheter 18. In order to provide a seal at the proximal portion 30 of the cannula body 26, the aperture 150 of the sealing plug 148 is sized to be in an interference fit with the shaft 74 of the balloon catheter 18. Further to that end, the sealing plug 148 includes a polymeric or elastomeric seal assembly 151. To allow easier traversal of the shaft 74 through the aperture 150, the balloon catheter 18 and/or the aperture 150 of the sealing plug 148 may include a lubricious coating or material. The balloon catheter 18 is then advanced distally relative to the cannula assembly 12 such that the dilator and the balloon 78 extend distally of the tip 28, to an illustrative position shown in FIGS. 2D and 2E.

The system 10 may then be flushed in order to prevent the introduction of air into the patient circulatory system once the delivery system 10 is deployed. In that regard, liquid is introduced, via a syringe, for example, into the second and third lumens 82b, 82c of the balloon catheter 18. Liquid is first introduced into the third lumen 82c and travels therethrough to the outlet 84 in fluid communication with the balloon interior, to thereby inflate the balloon 78 a sufficient amount that allows the balloon 78 to essentially seal the lumen 104 of the delivery sheath 20 at the distal portion 94. Liquid is then introduced into the second lumen 82b and travels therethrough and exits from the outlet 88, thus causing fluid to enter the lumen 34 of cannula body 26. Liquid flowing into the lumen 34 flows towards both the proximal portion 30 which is sealed by the sealing plug 148, and towards the distal portion 32 of the cannula body 26 whereby the fluid exits from the opening of the tip 28 and flows into the lumen 104 of the delivery sheath 20. The liquid in the lumen 104 of the delivery sheath 20 is prevented from flowing out of the distal portion 94 of the jaws 90 by the inflated balloon 78. Thus, an amount of liquid introduced into the third lumen 82c must be sufficient to fill the lumen 34 of the cannula body 26, as well as the lumen 104 of the delivery sheath 20 (including the cannula assembly 12 and balloon catheter 18 therein). The fluid(s) introduced into the second and third lumens 82b, 82c is (are) preferably saline, but may be other biocompatible fluids. The fluid introduced into the third lumen 82c, in one embodiment, may alternatively be a gas that is used to inflate the balloon 78.

Figure 4A:
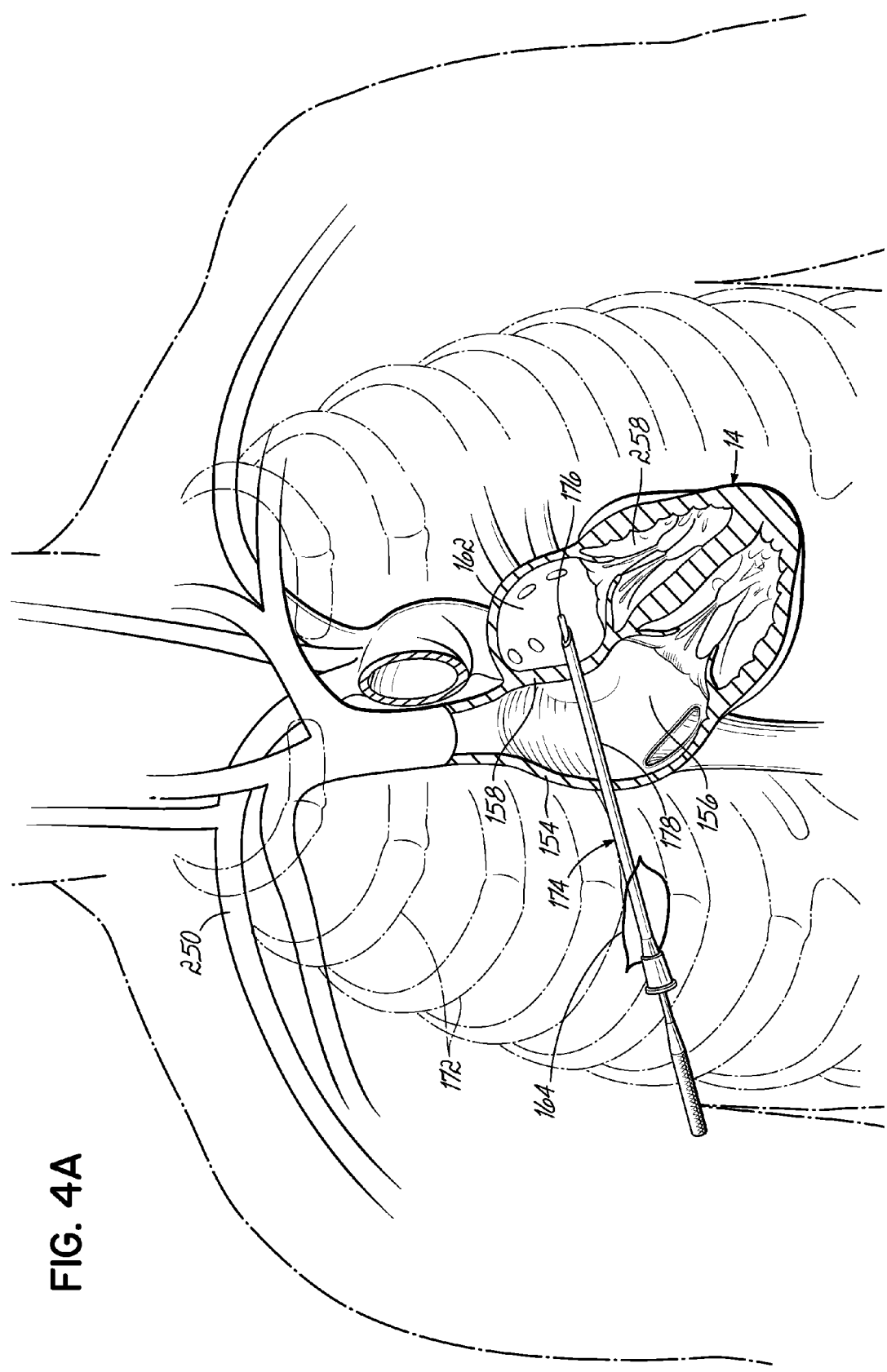
FIG. 4A is a diagrammatic view of an exemplary method of accessing the septum of the human heart, shown in cross section.
Figure 4B:
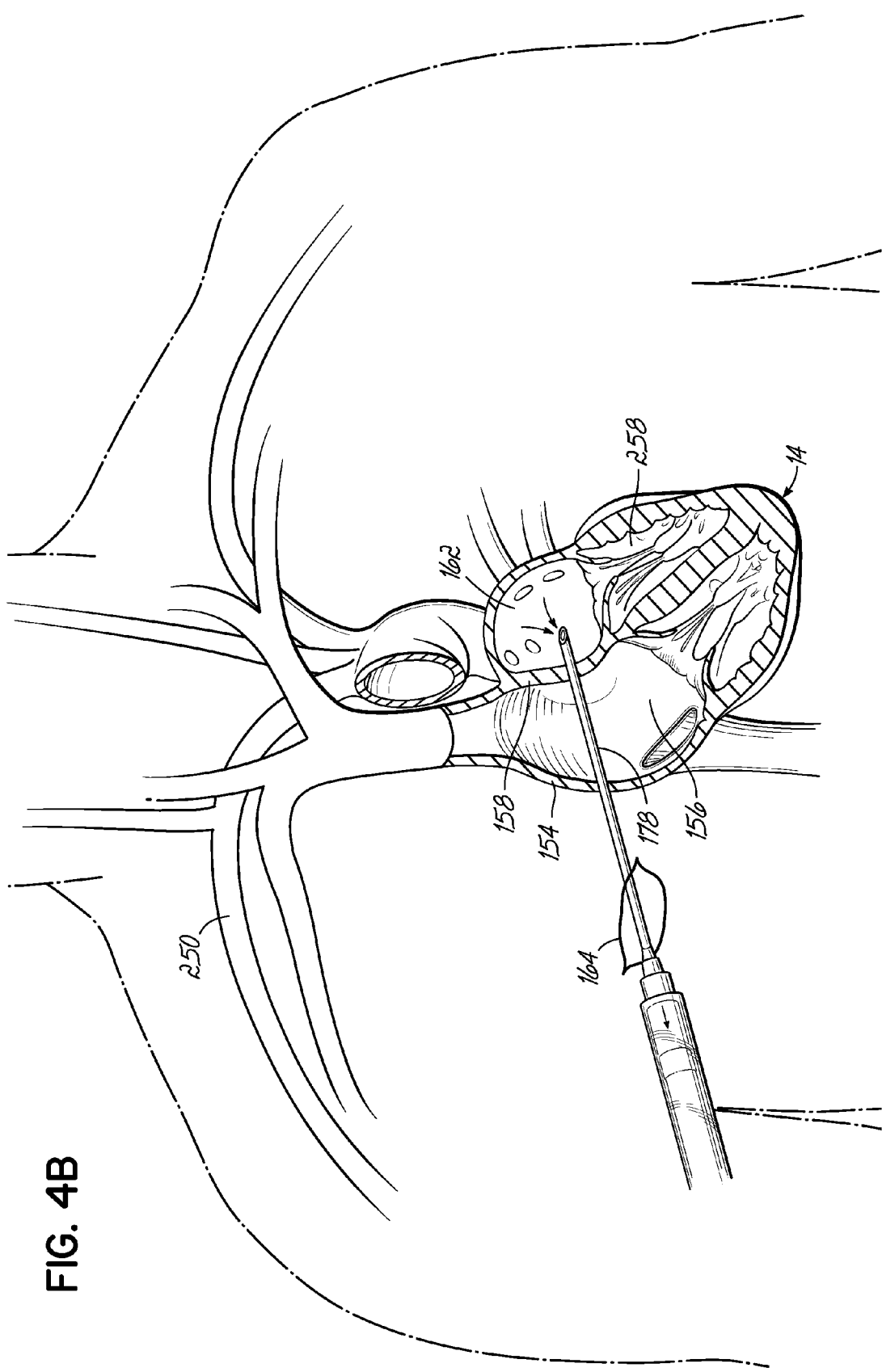
Figure 4C:
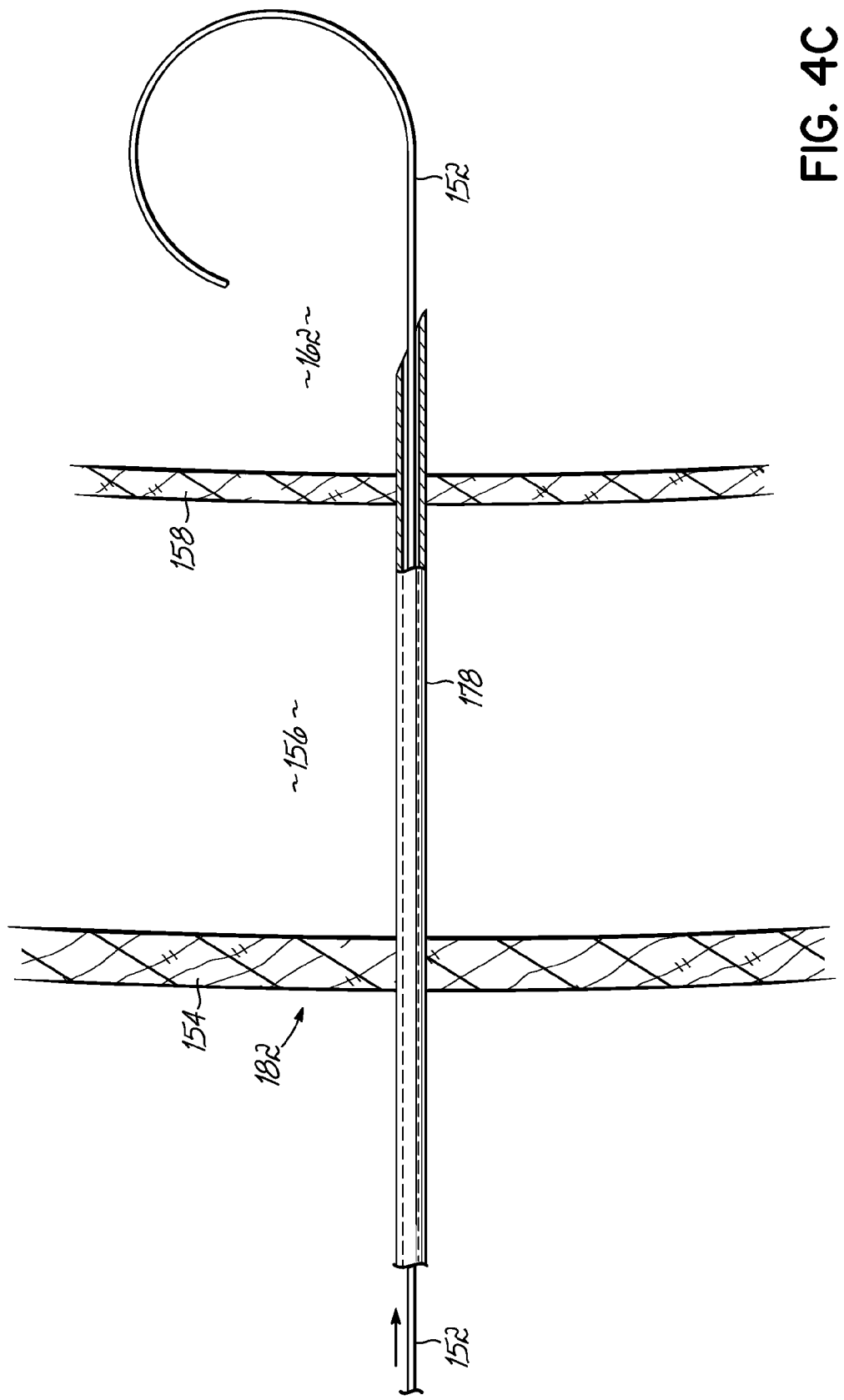
Figure 4D:
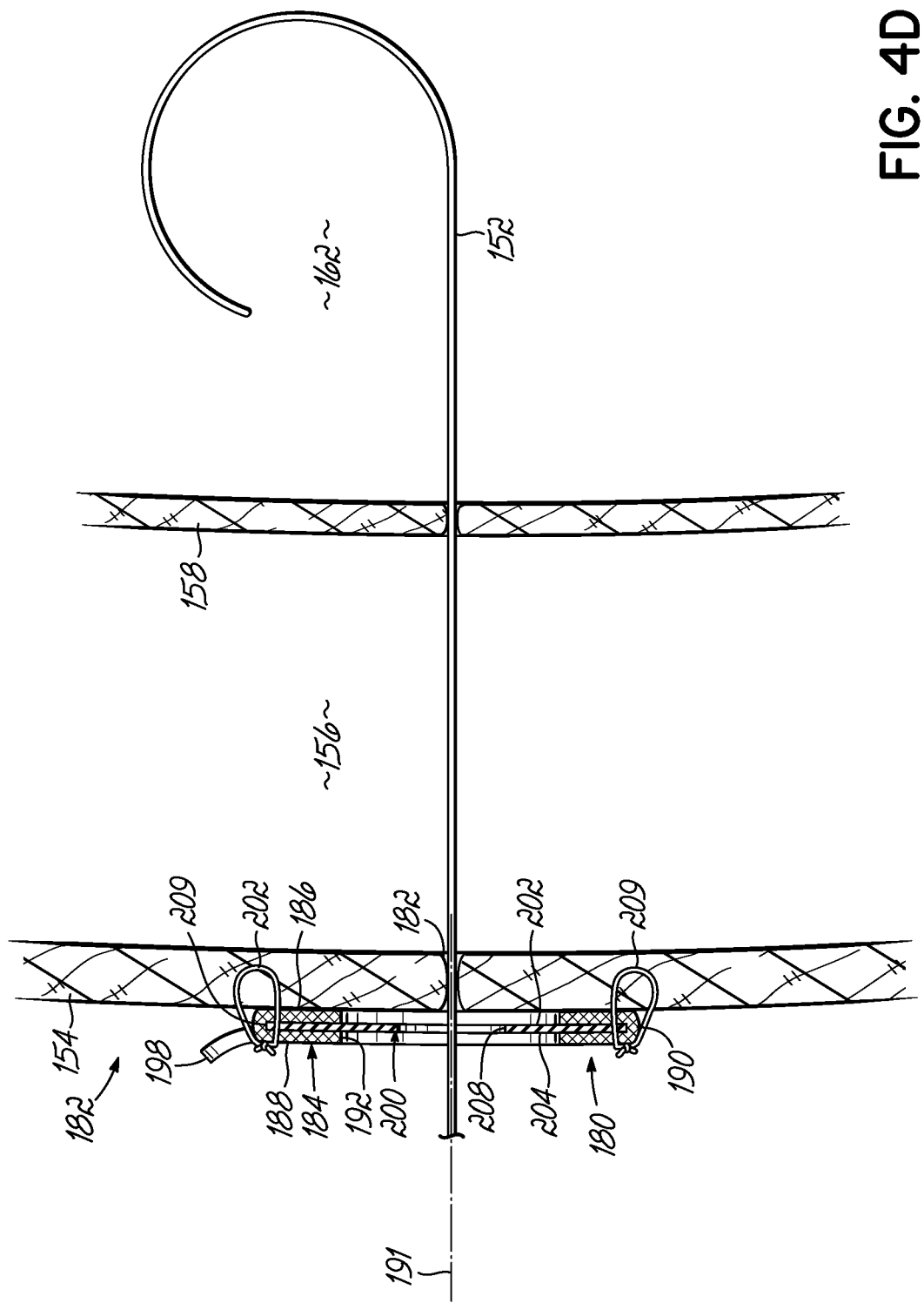
Figure 4E:
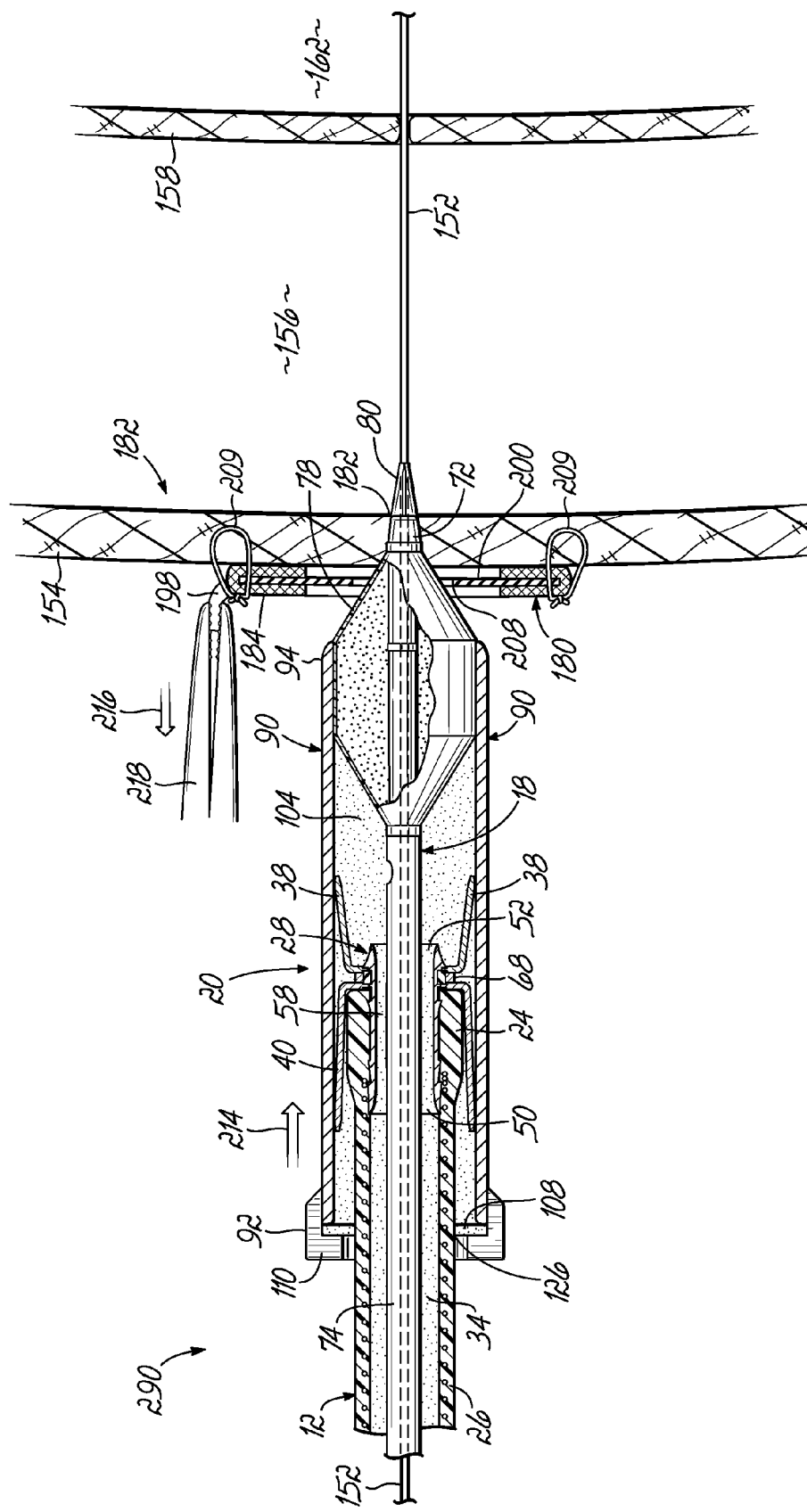

The surgeon, before, during, or after readying the delivery system 10, may begin the procedure used in implanting the circulatory assist system. In one embodiment, implanting the circulatory assist system can begin with a mini-thoracotomy procedure. FIGS. 4A-4N illustrate a portion of the procedure according to one embodiment that involves the placement of a guide-element, shown as a guidewire 152, through the right atrial wall 154, into the right atrium 156, and across the intra-atrial septum 158 of the heart 14 such that a distal portion of the guidewire 152 resides in the left atrium 162. The method begins with the surgeon making a primary incision site 164 (FIG. 4A) in the patient that is substantially near an intercostal space. While it is generally preferred that the incision 164 be made in the fourth (as shown), fifth, or sixth intercostal spaces, other points of access may be utilized, depending on the traits, such as size, of a specific patient.

Once the incision 164 is made, the surgeon or his/her staff spreads apart the ribs 172 adjacent the incision 164 in order to allow for access to the interior of the body, specifically, the thoracic cavity. The surgeon may then direct a piercing device 174 into the thoracic cavity, and through the right atrial wall 154 into the right atrium 156. In order to ensure proper placement, the piercing device 174 may include a flashback chamber (not shown) that provides a confirmation of access to the proper structure in the circulatory system, such as the right atrium 156. Moreover, because visualization within the thoracic cavity may be difficult, many of the steps described herein may be performed with assistance of an imaging technique, such as, for example, echocardiography ("echo"). As shown, the piercing device 174 includes an inner piercing stylet 176 that is movable relative to an outer hypotube 178. However, in other embodiments, the piercing device 174 may simply be a needle including a lumen and a sharp distal end. Once proper access through the right atrial wall 154 is confirmed, the surgeon further directs the piercing device 174 through the right atrium 156, and to and through the intra-atrial septum 158 such that a distal end of the piercing device 174 resides within the left atrium 162. Again, the surgeon ensures proper placement of the piercing device 174 and accordingly removes the piercing stylet 176 from the hypotube 178. The guidewire 152 is then directed into the lumen of the hypotube 178 until it reaches the position shown in FIG. 4C. The surgeon removes the hypotube 178 and the guidewire 152 remains in the position shown in FIG. 4C.

A first ring member 180 is then coupled to the right atrial wall 154. More particularly, referring to FIGS. 4D and 6B, the first ring member 180 is sewn to the right atrial wall 154 in a position generally concentrically relative to the access site where the guidewire 152 enters the right atrial wall 154.

The first ring member 180 is provided as reinforcement to the heart tissue surrounding the access site 182 and also may provide hemostasis between a component of the delivery system 10 and the heart wall. In that regard, the first ring member 180 includes an outer portion or layer 184 that is a generally annular, porous polymeric structure. The outer layer 184 may be one layer of the same polymer or fabric, or may be more than one layer of the same or different polymers or fabrics. The porous polymeric outer layer 184 allows for tissue in-growth, where tissue from the heart 14 may grow and embed within the porous polymeric structure to provide greater structural stability and sealing capacity.

The outer layer 184 is generally annular and includes a first side 186, a second side 188, a radially outer edge 190 circumscribing a central axis 191, and a radially inner edge 192. The inner edge 192 of the outer layer 184 defines an aperture circumscribing a central axis. The first aperture includes a cross-sectional dimension, particularly a diameter, that is sized and/or configured to allow the traversal of the delivery system 10. In one embodiment, the diameter of the aperture is larger than the outer diameter of the delivery sheath 20 in the closed configuration. The first ring member 180 also includes a tab 198, or gripping portion, extending radially from the outer edge 190. The tab 198 may be grasped and pulled in order to provide a counter force (i.e., pulling) when inserting or directing (i.e., pushing) the delivery system 10 through the ring member and through the external heart wall.

The first ring member 180 includes an inner portion or layer 200 having portions that are positioned both axially inward and radially inward relative to the outer layer 184. As shown, the outer layer 184 essentially encapsulates at least a portion of the inner layer 200. More particularly, the inner layer 200 includes a first side 202, a second side 204, a radially outer edge 206, and a radially inner edge 208, both surrounding the central axis (essentially defined by guidewire 152). The outer edge 206 of the inner layer 200 is positioned radially inward of the outer edge 190 of the outer layer 184. The inner edge 208 of the inner layer 200 defines a radially inner second aperture, and is positioned radially inward of the outer and inner edges 190, 192 of the outer layer 184. The inner and outer layers 184, 200 are positioned generally concentrically relative to one another. The inner layer 200 provides reinforcement in addition to that provided by the outer layer 184, while also being configured to assist in providing hemostasis (i.e., a seal) between the heart tissue and components of the delivery system 10.

In that regard, the inner layer 200 may comprise a polymeric or rubber-like material such as silicone, urethane, etc., that include pliability and resiliency features to allow for hemostasis when components of the delivery system 10 are directed through the first and second apertures and into the heart 14. Further to that end, the cross-sectional dimension, such as diameter, of the inner second aperture must be sized to be in an interference fit with components of the delivery system 10, including, but not limited to, the delivery sheath 20 and the flexible cannula assembly 12. As described herein, the first ring member 180 is preferably coupled to the heart tissue prior to any components of the delivery system 10 being directed into the heart tissue.

Figure 2E:
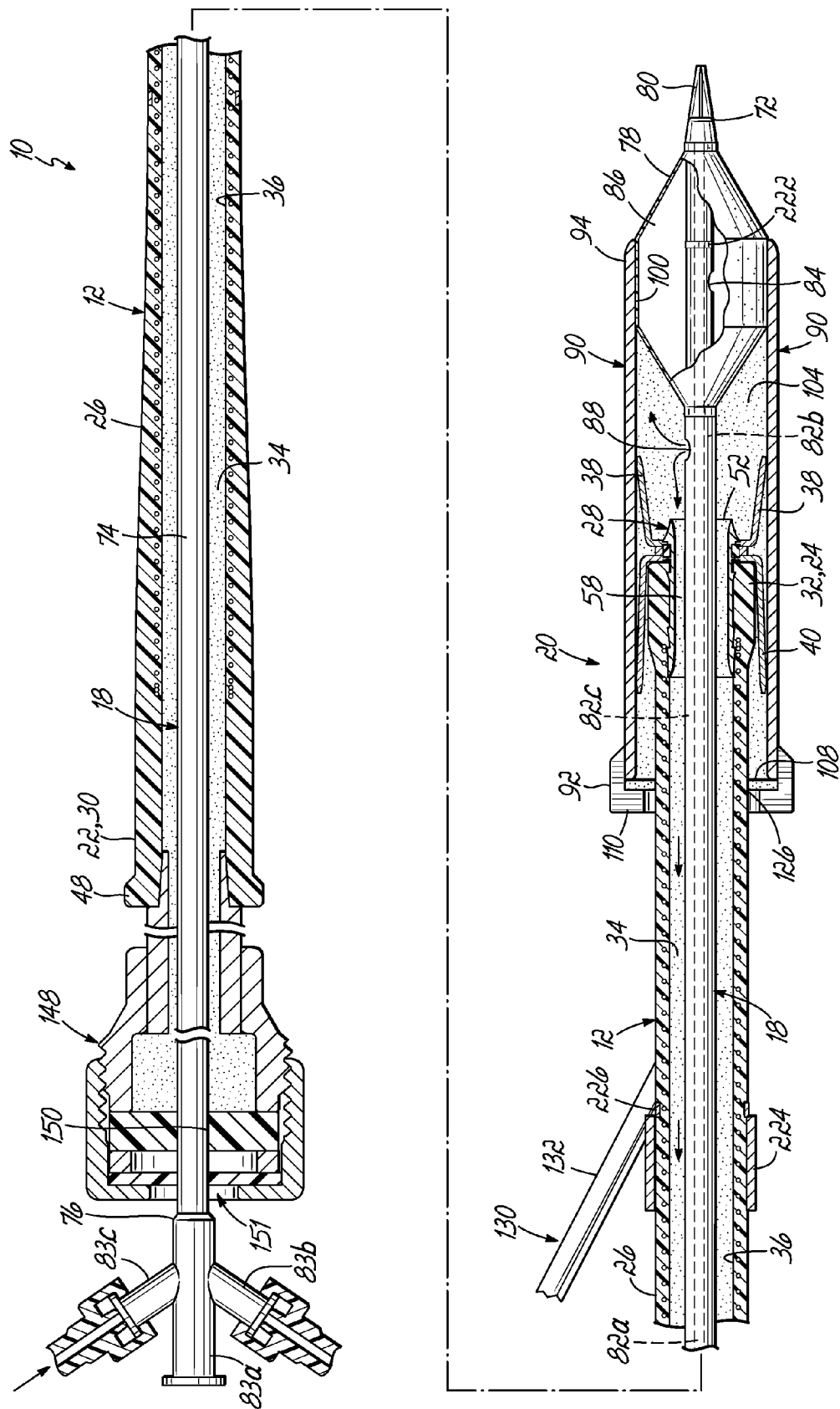
Figure 3C:
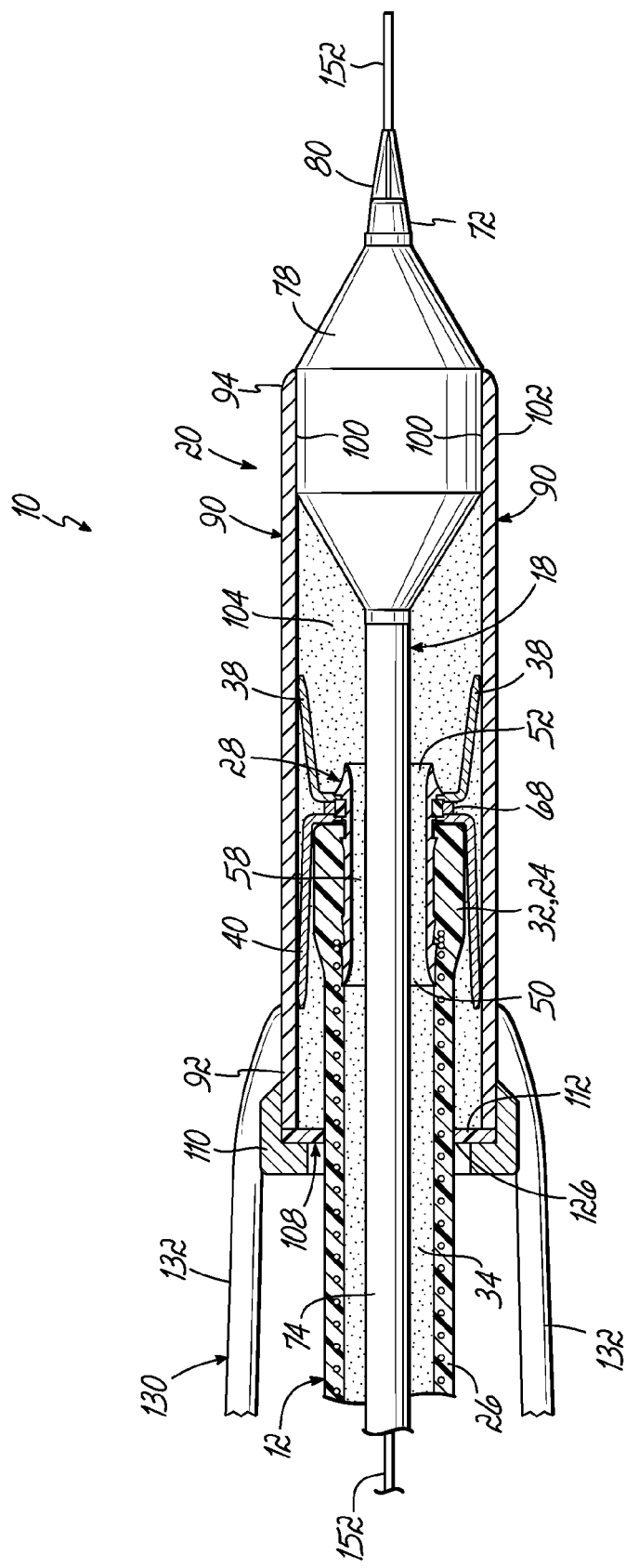
FIG. 3C is a top view in partial cross section showing the delivery system assembled for purposes of being directed to the heart.

Once the guidewire 152 is deployed and the first ring member 180 is coupled by sutures 209 to the heart 14, the delivery system 10 in the assembled position, and flushed, as shown in FIGS. 2E and 3C, may then be traversed over the guidewire 152.

More particularly, once the system 10 is assembled and flushed, the balloon catheter 18, the cannula assembly 12, and the delivery sheath 20, as a unit, are positioned over the proximal end (not shown) of the guidewire 152 such that guidewire 152 is backloaded into the first lumen 82a of balloon catheter 18. Thus, the entire system 10 is backloaded onto the guidewire 152. Once backloaded onto the guidewire 152, the delivery system 10 is directed into the thoracic cavity through the fourth intercostal space 166.

Referring to FIGS. 4E-4N, the balloon catheter 18, with the cannula assembly 12 and the delivery sheath 20, will follow the wire to the outer portion of the right atrial wall 154 to a position whereby the system 10 is positioned generally concentrically relative to the ring member 180. Once the assembled system 10 reaches the outer portion of the right atrial wall 154, the obturator tip 80 may enter the access point 182 through which the guidewire 152 extends and dilate the tissue. As the system 10 is pushed further into the heart 14, the obturator tip 80, as well as a proximal cone of the balloon 78, further dilate the heart tissue to create an opening sufficient to allow for the passage of the delivery sheath 20 and the cannula assembly 12.

The interference fit between the first ring member 180 and the delivery sheath 20 may inevitably lead to friction between these components. Thus, as the delivery sheath 20 is pushed through the apertures of first ring member 180, the right atrial wall 154 itself may be forced inwardly (to the right as shown in FIG. 4E, indicated by arrow 214), which may be undesired in some circumstances. To counteract such an occurrence, the surgeon may pull on the tab 198 of first ring member 180 in the direction away from the heart 14 (indicated by arrow 216). Thus, the surgeon provides a force that essentially opposes the pushing force associated with directing the system 10 through the heart wall. Because the ring member 180 is sutured to the right atrial wall 158 around the access site 182 at several locations (FIG. 6B), the pulling force is distributed across the ring member 180 and thus a larger surface area of the heart wall. The surgeon may pull on the tab 198 with either his fingers or an instrument 218 as shown.

Figure 4F:
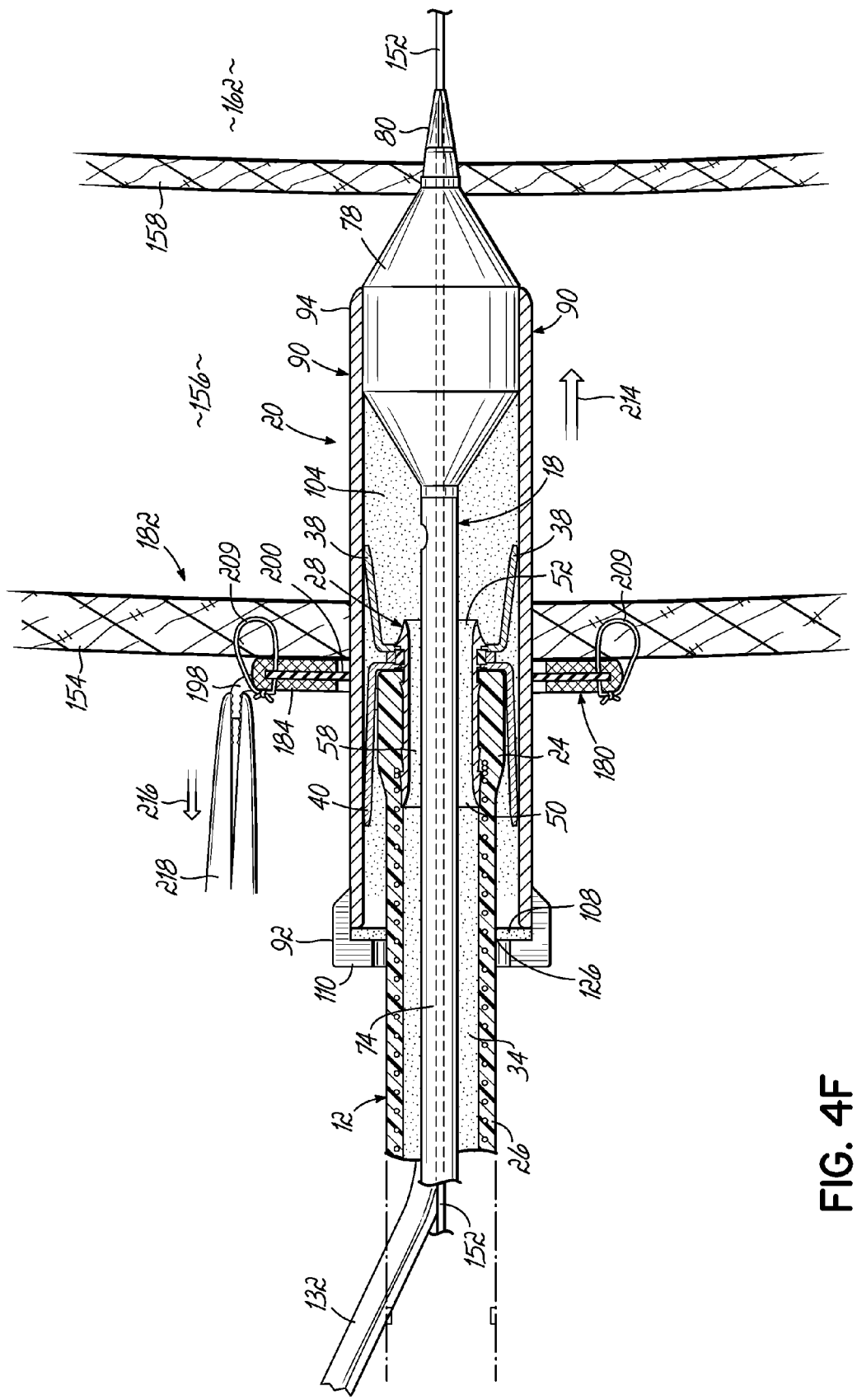

Referring now to FIG. 4F, the system 10 has been traversed partially through the right atrial wall 154 such that the distal portions 94 of the jaws 90 reside within the right atrium 156, and the obturator tip 80 has begun to dilate the intra-atrial septum 158, in a manner similar to that just discussed with respect to the right atrial wall 154. The system 10 may traverse through the intra-atrial septum 158 at any point of the intra-atrial septum 158, including the fossa ovalis. As shown, the distal portion 24 of the cannula assembly 12 has been introduced through the outer portion of the right atrial wall 154, and advanced past an inner portion of the right atrial wall 154.

Figure 4G:
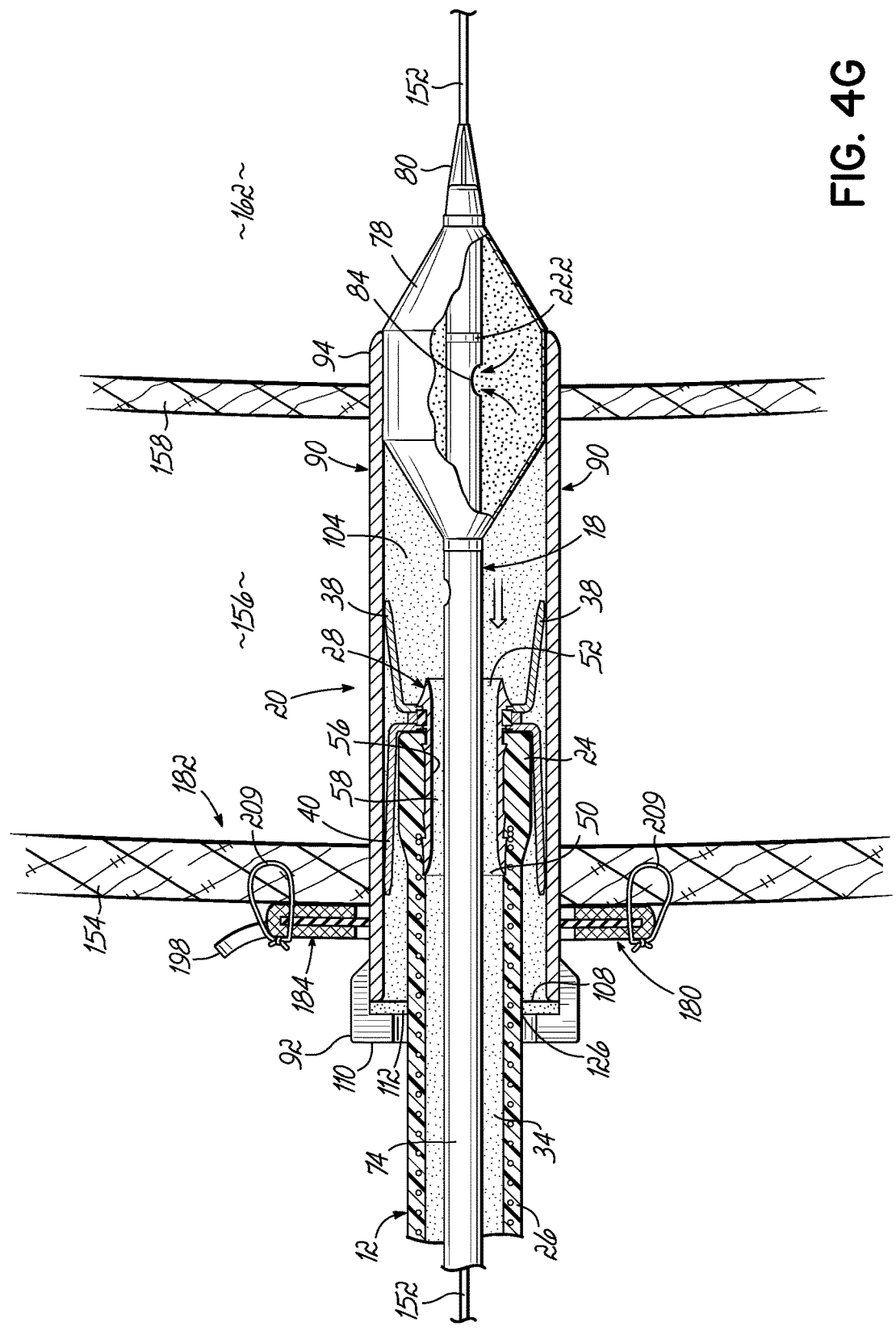

Referring to FIG. 4G, the system 10 is further directed into the heart 14 until the distal portion 94 of the jaws 90 resides within the left atrium 162. Thus, the cannula assembly 12 now has access to the left atrium 162 via the lumen 104 of the delivery sheath 20. In order to deploy the flexible cannula assembly 12, the balloon 78 is deflated and retracted distally to a position shown in FIG. 4H. The surgeon may use marker band 222 (visualized on echocardiography, for example) on each of the tip 28 and the balloon 78 (FIGS. 4H-4I) in order to assist in properly positioning the balloon 78 relative to the tip 28. The balloon 78 is then inflated to engage the inner wall 56 of the tip, thus preventing relative movement between the balloon catheter 18 and the tip 28, but still permitting relative movement between the tip 28 and the delivery sheath 20.

Figure 4I:
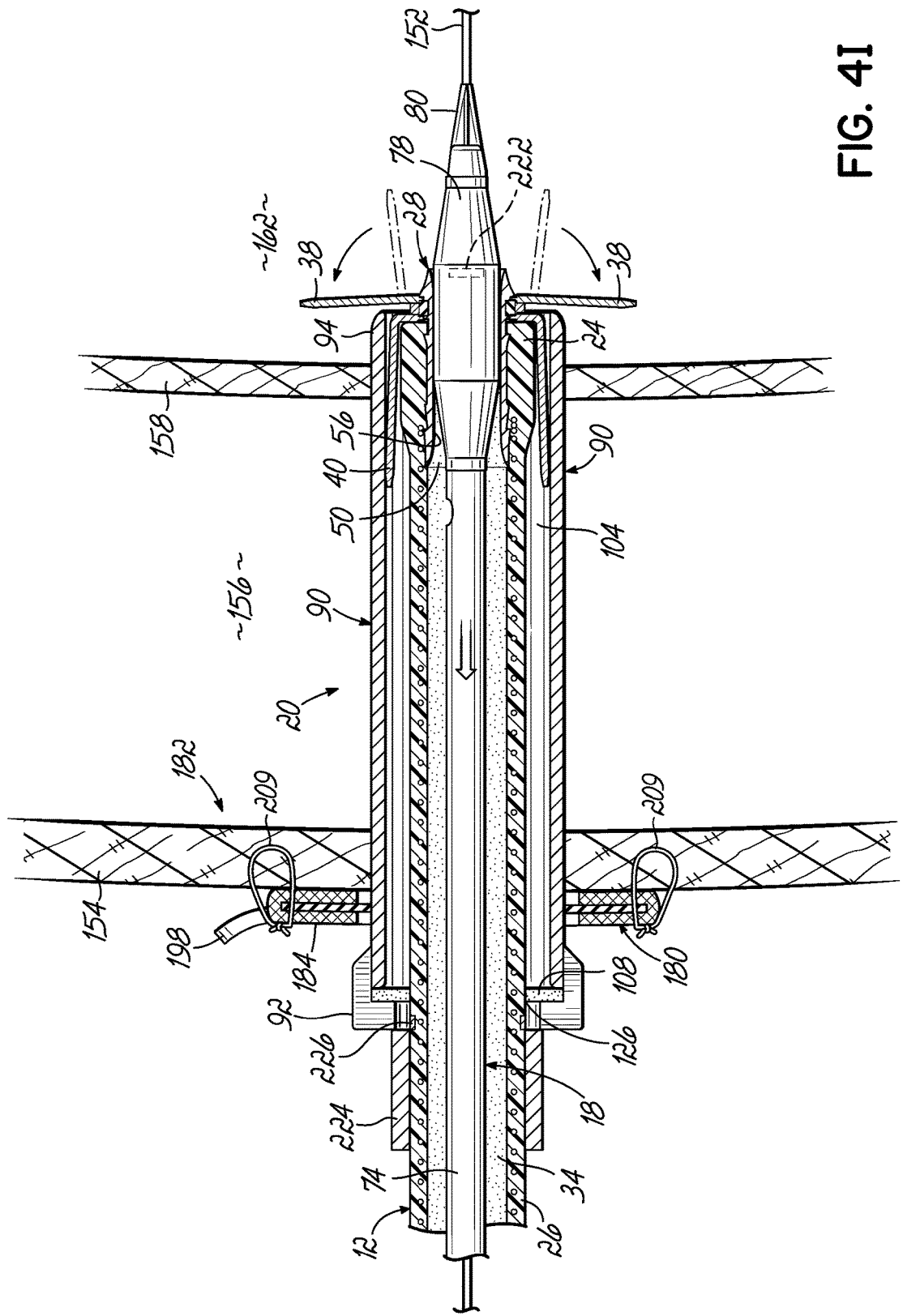

In FIG. 4I, the surgeon advances the balloon catheter 18 with the tip 28 beyond the delivery sheath 20, such that the first anchor 38 is moved beyond the delivery sheath 20 and into the left atrium 162. In this way, the first anchor 38 is deployed (sprung outward) from the contracted state (in phantom) to the deployed state (in solid) within the left atrium 162. The second anchor 40 remains in the contracted state and within the delivery sheath 20. In order to allow for a predetermined amount of distal movement of the flexible cannula assembly 12 relative to the delivery sheath 20, that allows for only the first anchor 38 to be deployed into the left atrium 162, and prevents the second anchor 40 from being deployed into the left atrium 162, a removably attachable stop member 224 may be applied to the cannula body 26. In that regard, the stop 224 may be removably coupled to the cannula body 26 at a position where the stop 224 contacts the proximal portion 92 of the delivery sheath 20 after moving a predetermined amount or distance relative to the delivery sheath 20. More particularly, the stop 224 may contact the delivery sheath 20 once the cannula assembly 12 has moved the predetermined amount where only the first anchor 38 has exited from the delivery sheath 20, but the second anchor 40 remains positioned within the delivery sheath 20. Thus, in preventing the further distal movement of the cannula assembly 12, the second anchor 40 is prevented from being inadvertently deployed within the left atrium 162. To allow for accurate placement of the stop member 224 in order to provide for the predetermined amount of movement, the cannula body 26 may include a visual marker 226 where the stop member 224 is to be placed. The visual marker 226 may be embedded within the cannula body 26, printed on the cannula body 26, or may be a separate component essentially wrapped around the cannula body 26.

Figure 4J:
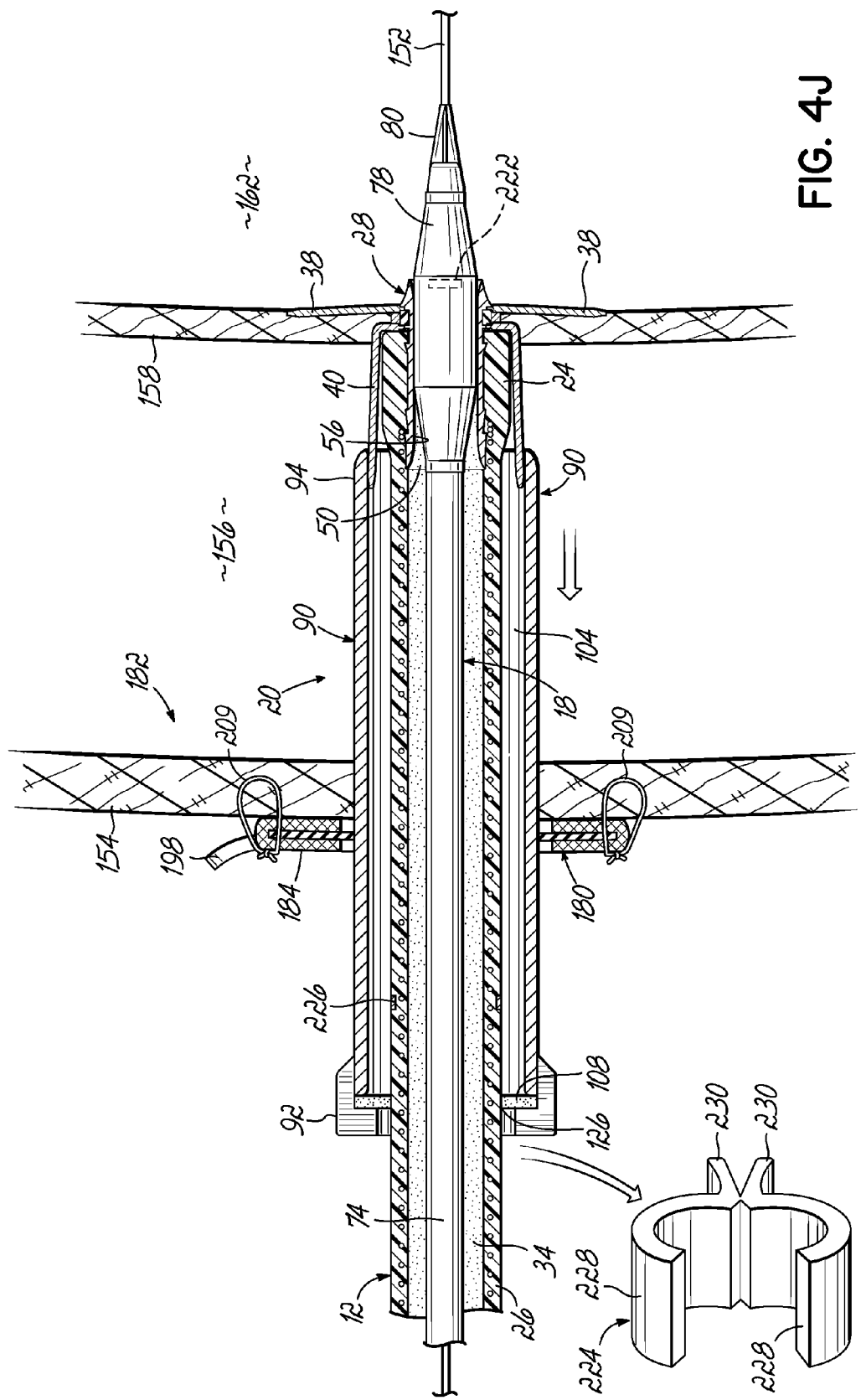

FIG. 4J illustrates the retraction of the balloon catheter 18 along with the tip 28 and the delivery sheath 20 until the deployed first anchor 38 contacts the intra-atrial septum 158 within the left atrium 162, and the distal portion 24 is positioned adjacent to the intra-atrial septum 158. To allow the proximal movement of the delivery sheath 20, the stop member 224 is removed from the cannula body 26. As shown, the stop member 224 includes two curved arms 228 that are hingedly coupled to one another, and two gripping portions 230 that may be moved relative to one another in order to open and close the arms. The configuration of the stop member 224, however, is not so limited.

Figure 4K:
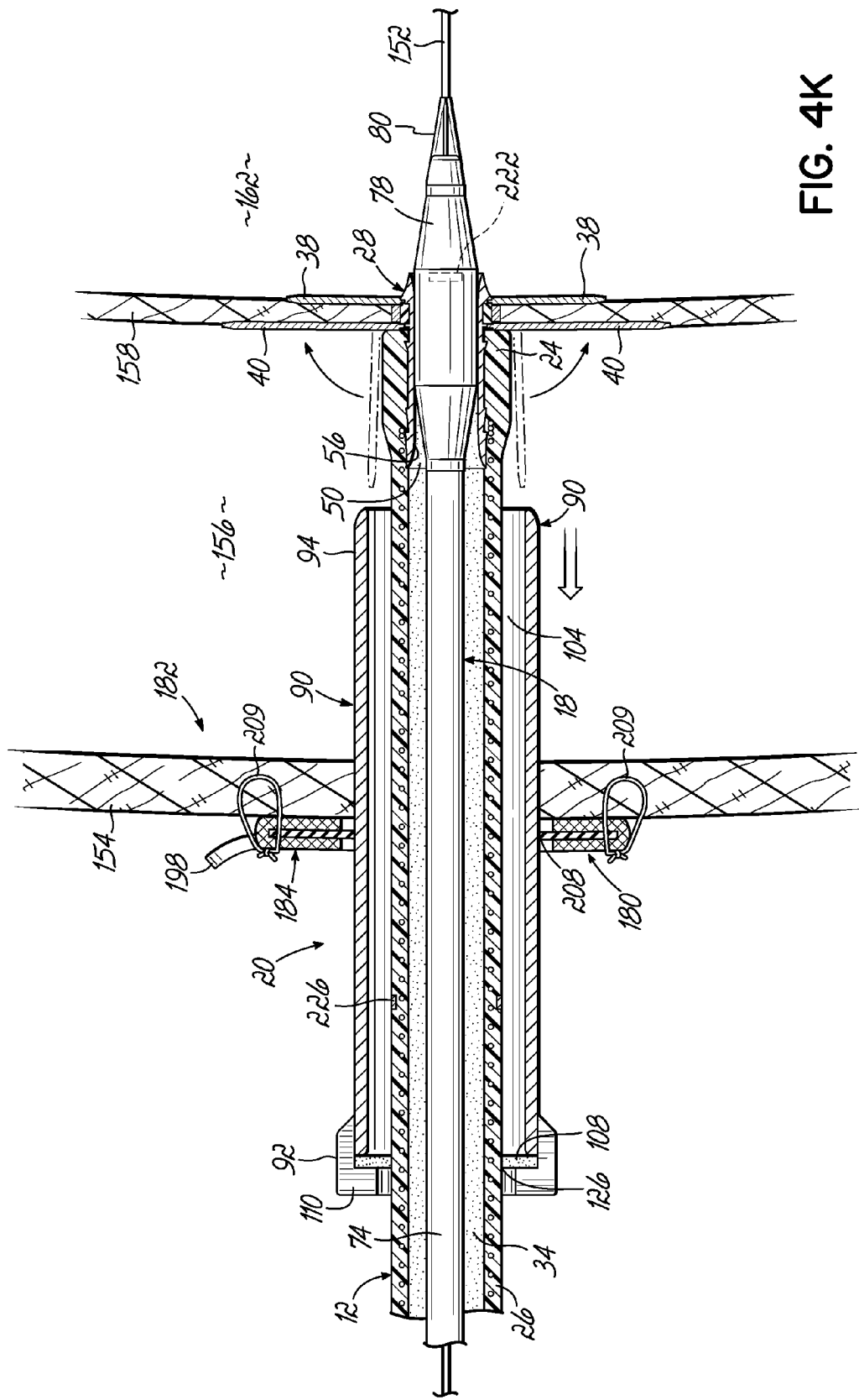

As shown in FIG. 4K, the surgeon continues to retract the delivery sheath 20 in the direction of the arrow while balloon catheter 18 and the tip 28 are maintained in position. This deploys the second anchor 40 in a manner similar to the first anchor 38, from a contracted position to an expanded position. Together, the first and second anchors 38, 40 secure the distal portion 24 of the cannula assembly 12 to the intra-atrial septum 158 and will prevent movement of the tip 28 from the intra-atrial septum 158.

Figure 4L:
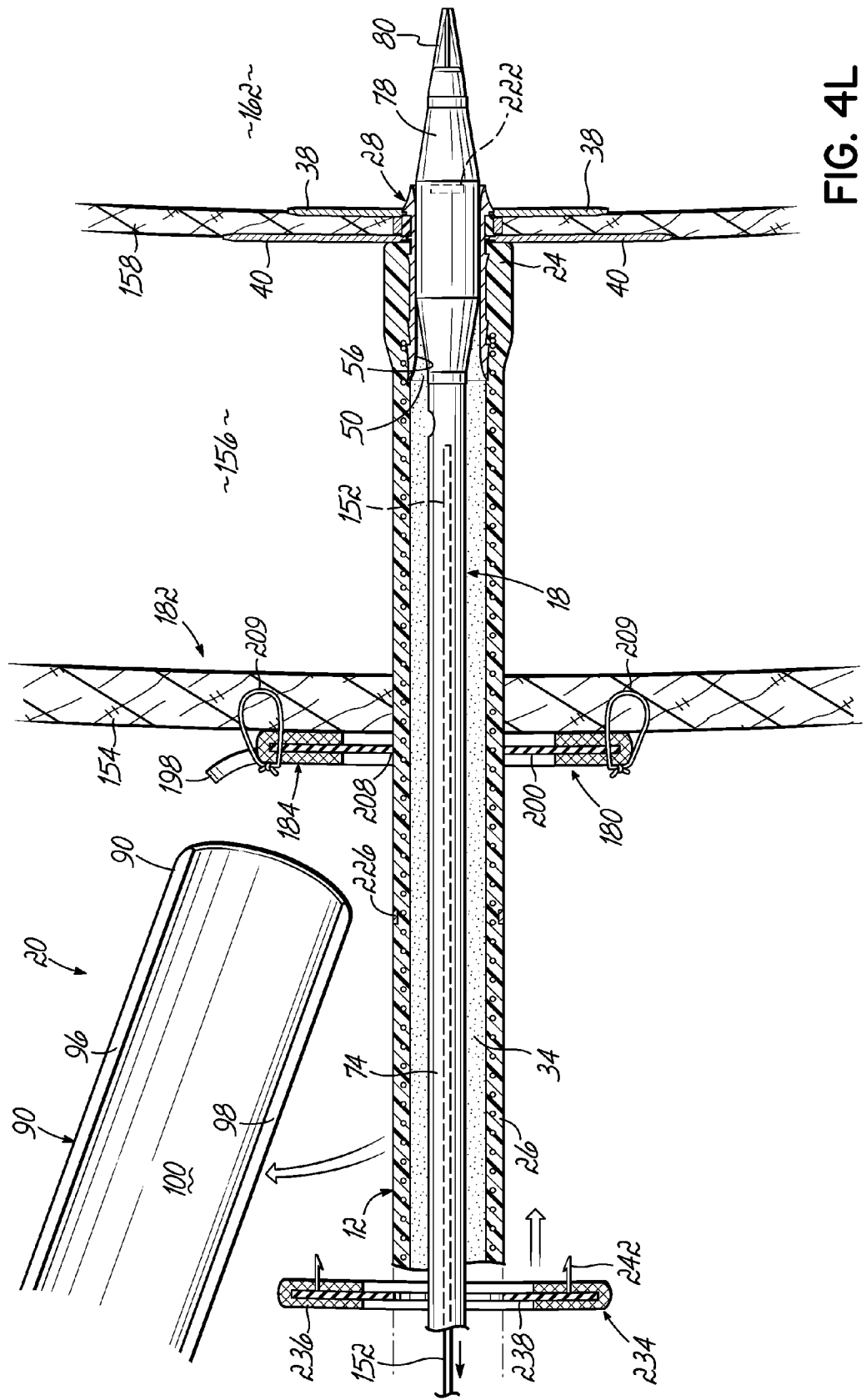
Figure 4M:
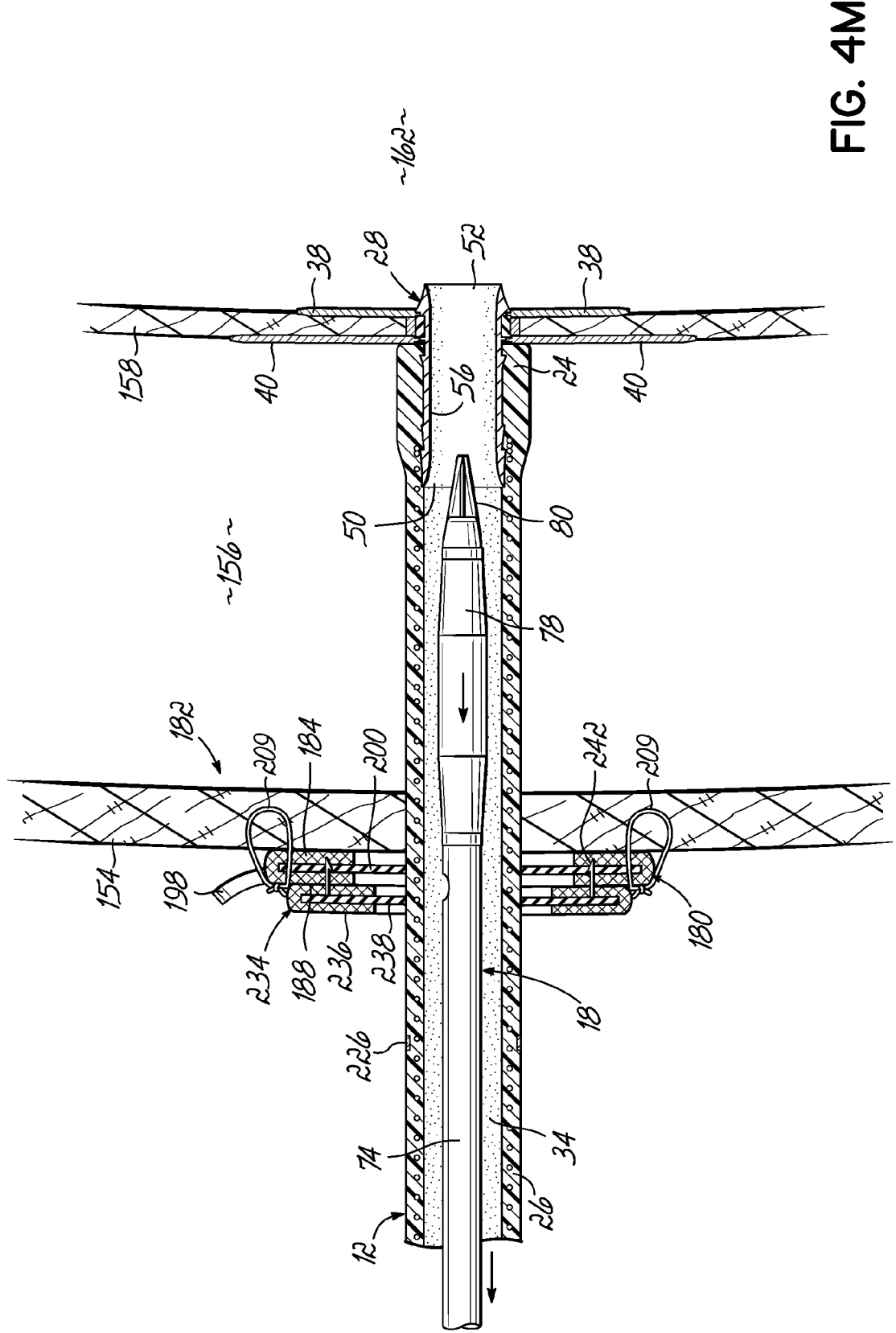
Figure 4N:
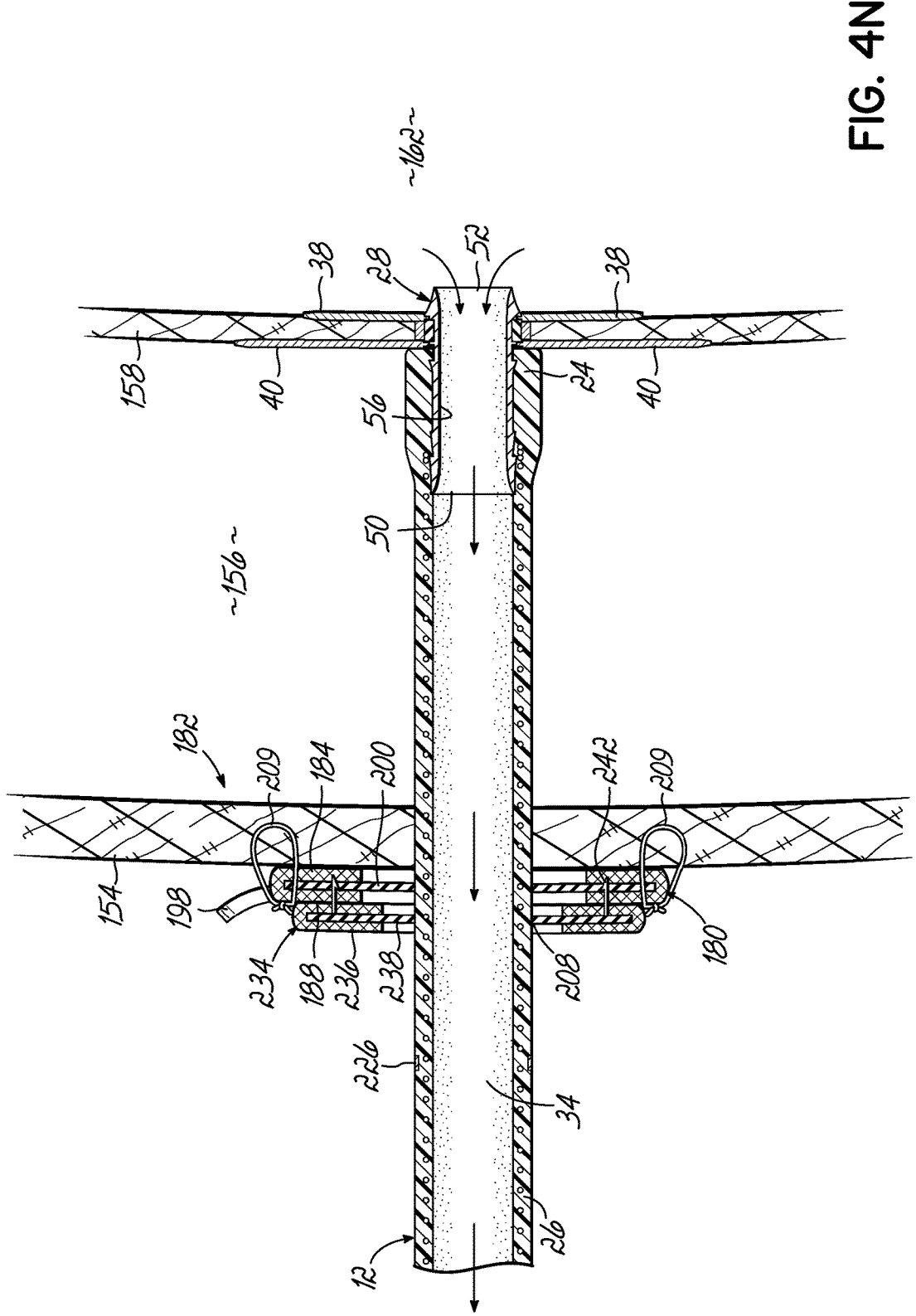

Now that the tip 28 and the anchors are implanted on opposite sides of the intra-atrial septum 158, the delivery sheath 20 can then be removed from the heart 14, through the thoracic cavity, and out of the mini-thoracotomy incision 164. Referring to FIGS. 4K and 4L, initially, the delivery sheath 20 is retracted with the jaws 90 in the closed configuration, in the direction of arrow. Because the largest outer cross-sectional dimension (i.e., the diameter) of the cannula body 26 (i.e., at the proximal section) is larger than the cross-sectional dimension (i.e., diameter) of the lumen 104 of the delivery sheath 20, the jaws 90 must be opened in order for the delivery sheath 20 to be retracted fully. More specifically, once the proximal portion 92 of the jaws 90 substantially contacts or approaches the portion of the cannula body 26 having the larger diameter, the surgeon opens the jaws 90 to further retract the delivery sheath 20 relative to the flexible cannula assembly 12. Prior to moving the jaws 90 to the open configuration, the locking mechanism 146 is unlocked by the surgeon, if the jaws 90 were locked. Then, once the delivery sheath 20 is retracted relative to the cannula assembly 12, it may be removed from the thoracic cavity, out of the incision 164. The jaws 90 may or may not need to be moved to or towards the closed configuration in order to remove the delivery sheath 20 from the incision 164.

After the delivery sheath 20 is removed, the balloon catheter 18 may be removed. The surgeon deflates the balloon catheter 18 enough to allow movement of the balloon catheter 18 within the lumen 34 of the cannula body 26. The surgeon then pulls the balloon catheter 18 in the direction of arrow until the balloon catheter 18 exits from the cannula whereby it may be further pulled out of the thoracic cavity through the incision 164. The guidewire 152 may be removed concurrently with the balloon catheter 18, or before or after the guidewire 152 is removed. The cannula body 26 is then clamped in order to prevent blood flowing from the left atrium 162, into the lumen 34 of cannula body 26, and out of the proximal portion 30 of the cannula body 26.

In some embodiments, it may be advantageous to provide additional hemostasis between the access site 182 in the right atrial wall 154 and the cannula body 26, and also to provide additional support for the heart wall and the cannula body 26. In that regard, referring to FIGS. 4L-4N and 6A-6B, a second ring member 234 may be deployed relative to the cannula assembly 12 and the right atrial wall 154. More particularly, the second ring member 234 is deployed around the cannula and coupled to the first ring member 180. The second ring member 234 is constructed similarly to the first ring member 180. In that regard, the second ring member 234 includes an outer layer 236 and an inner layer 238, in a manner substantially similar to that described above with respect to the first ring member 180, except that it does not include a tab 198, and generally includes a smaller cross-sectional area than the first ring member 180, in the embodiment shown.

Second ring member 234 includes a split portion 235 (FIGS. 6A and 6B) that allows the second ring member 234 to be positioned around the cannula body 26 at an intermediate portion thereof, in the event that the diameter of aperture is smaller than the largest outer diameter of the flexible cannula assembly 12.

Figure 6A:
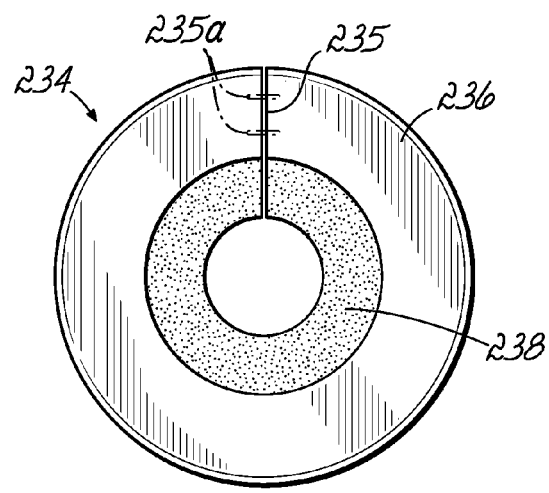
FIG. 6A is a front plan view of a ring member according to one embodiment of the invention.
Figure 6B:
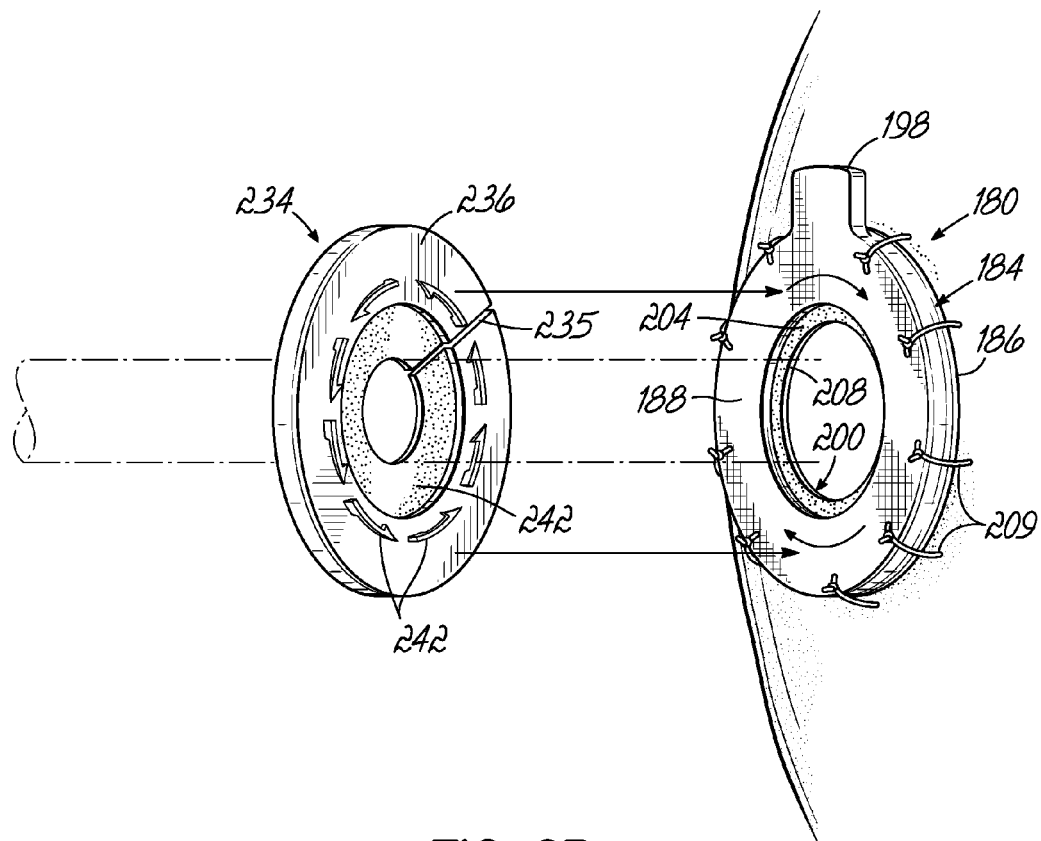
FIG. 6B is a perspective view of an exemplary method of fixing the ring member of FIG. 6A to another ring member.

In order to couple the second ring member 234 to the first ring member 180, the second ring member 234 includes barbs 242 on one side thereof. The second ring member 234 is first placed around the cannula body 26, by separating the split portion. The surgeon may then couple each end of the second ring member adjacent the split, preferably with sutures 235a. The second ring member 234 may then be directed distally along the cannula until the barbs contact the second side 188 of first ring member 180. The second ring member 234 may then be pushed distally against the first ring member 180 and rotated in a direction (clockwise as shown in FIG. 6B) which will allow the barbs 242 to positively engage the first ring member 180. Once the barbs 242 are positively engaged with the first ring member 180, the barbs 242 prevent axial or rotational motion of the second ring member 234 relative to the first ring member 180. Alternatively, the second ring member 234 may be coupled to the first ring member 180 by suturing or another method of coupling. Although it may be advantageous to position the ring around the cannula body 26 after the delivery sheath 20 and other components have been retracted, it is possible to position the second ring member 234 about the cannula body 26 prior to the deployment of any of the components of the delivery system 10. As described herein, the first ring member 180, the second ring member 234, and/or the cannula assembly 12 may include features for attaching a cannula assembly 12 relative to a ring member, such as those described in U.S. Patent Application Publication No. 2013/0060267 (the '267 publication) assigned to the assignee of the present invention, filed Sep. 4, 2012, and entitled CANNULA TIPS, TISSUE ATTACHMENT RINGS, AND METHOD OF DELIVERING THE SAME. The '267 Publication is hereby incorporated herein by reference.

After the flexible cannula assembly 12 has been implanted in accordance with one of the methods described previously, and all assistant devices (guidewire 152, delivery cannula, balloon obturator, etc.) have been removed, the other components of the circulatory assist system can be implanted. Before the proximal portion 30 is connected to the pump inlet, the proximal portion of the cannula body 26 may reside within the thoracic cavity, near the fourth, fifth, or sixth intercostal spaces. Thus, the proximal portion of the cannula body 26 must be directed to the pump pocket, which is a submuscular or subcutaneous space that may be positioned generally at or near the second intercostal space. In one embodiment, the proximal portion of the cannula body 26 and the inlet of the blood pump 16 may be coupled in situ, according to the teachings of U.S. Provisional Application Ser. No. 61/839,580 (the '580 application), assigned to the assignee of the present invention and entitled SYSTEM AND METHOD OF FACILITATING CONNECTION BETWEEN CANNULAE AND A BLOOD PUMP. The '580 application is hereby incorporated herein by reference.

FIG. 1 shows the circulatory assist system fully implanted. In that regard, the proximal end 30 of cannula body 26 is attached to the inlet of the pump 16. A separate outflow cannula 248 is attached to the outlet of the pump 16, which is then surgically attached so as to communicate with a suitable superficial artery, such as the right subclavian artery 250. At this time, the surgeon may position the implantable pump 16 in the pump pocket, or maintain the pump 16 externally even after the secondary incision site, that provides access to the pump pocket, is closed. The pump 16 may be operably associated with a controller (not shown), which may also be implanted or remain external to the patient.

In one embodiment of the method shown and described herein, the distal portion 24 of the cannula assembly 12 resides in the left atrium 162 such that the tip 28 is in fluid communication with the left atrium 162. The cannula assembly 12 extends from the left atrium 162, through the intra-atrial septum 158, through the right atrium 156, and through and out the right atrial wall 154, whereby the proximal portion 22 of the cannula assembly 12 may be connected to the inlet of the pump 16 as described herein. Thus, as shown, the distal portion 24 of the cannula assembly 12, including the tip 28 has been introduced through an outer portion of an external wall (right atrial wall 158) of the heart 14 such that the tip is in fluid communication with a first chamber, the right atrium 156. The cannula assembly is then advanced through the external wall and past an inner portion of the external wall opposing the inner portion. The distal portion 24 of the cannula assembly 12 has been further advanced relative to the heart 14 and through an internal structure of the heart 14, the intra-atrial septum 158, such that the tip is in fluid communication with a second chamber, the left atrium 162. Finally, the tip has been secured to the intra-atrial septum 158 using the anchors 38, 40 as described herein.

In other embodiments, the cannula assembly 12 may be secured to the heart 14 for directing blood from the heart 14 in different manners. For example, in an alternative embodiment, the cannula assembly 12 may be introduced through the right ventricular wall and advanced through the right ventricle to the intra-ventricular septum, and secured to the intra-ventricular septum with the tip 28 and lumen 34 of cannula body 26 being in fluid communication with the left ventricle. The cannula assembly 12 may be secured to the intra-ventricular septum in a similar manner as the securement to the intra-atrial septum 158 as described hereinabove. In another alternative embodiment, the cannula assembly 12 may be introduced through a superior portion of the left atrium 162. The distal portion 24 of the cannula assembly 12 may then be advanced through the left atrium 162 and through the mitral valve such that the tip 28 and lumen 34 of cannula body 26 are in fluid communication with the left ventricle 258. The distal portion 24 may then be secured to the mitral valve. In yet another alternative embodiment, the cannula assembly 12 may be introduced through left ventricular wall at or near the apex of the heart 14. The distal portion 24 of the cannula assembly 12 may then be advanced through the left ventricle 258 and through the mitral valve such that the distal portion 24 is in fluid communication with the left atrium 162. The distal portion 24 may then be secured to the mitral valve.

In order to accommodate for patients of different sizes, the current state of the art provides the surgeon with a longer than necessary cannula that must be cut to the desired length. In cutting the cannula to length, the surgeon runs the risk of cutting it improperly or damaging the cannula, which may compromise the connection between the cannula and the pump inlet, or may require the surgeon to remove the deployed cannula and go through the lengthy process of deploying another cannula.

Figure 8:
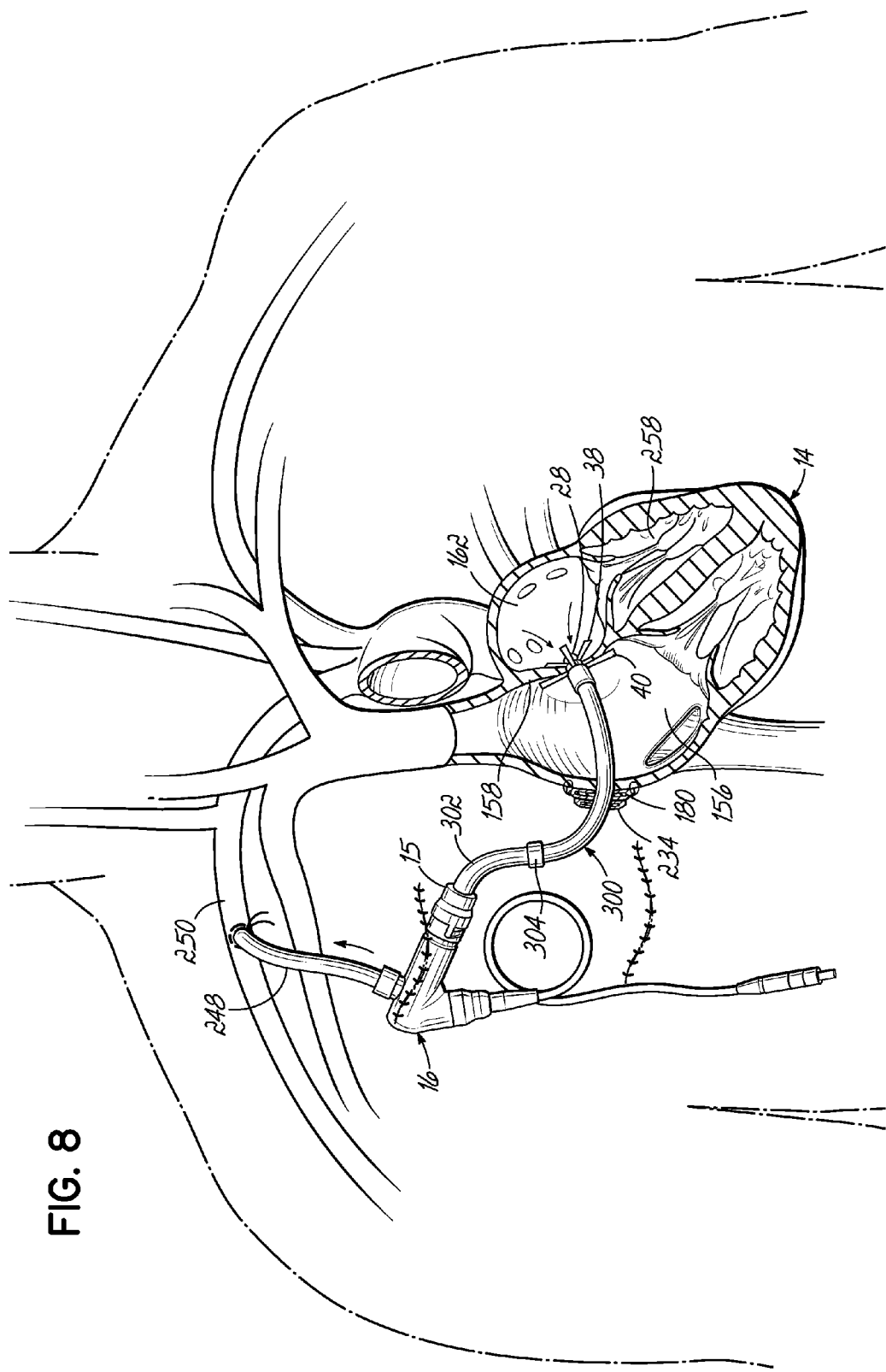
FIG. 8 is a diagrammatic view of an alternative embodiment of a circulatory assist system implanted in the patient.
Figure 9:
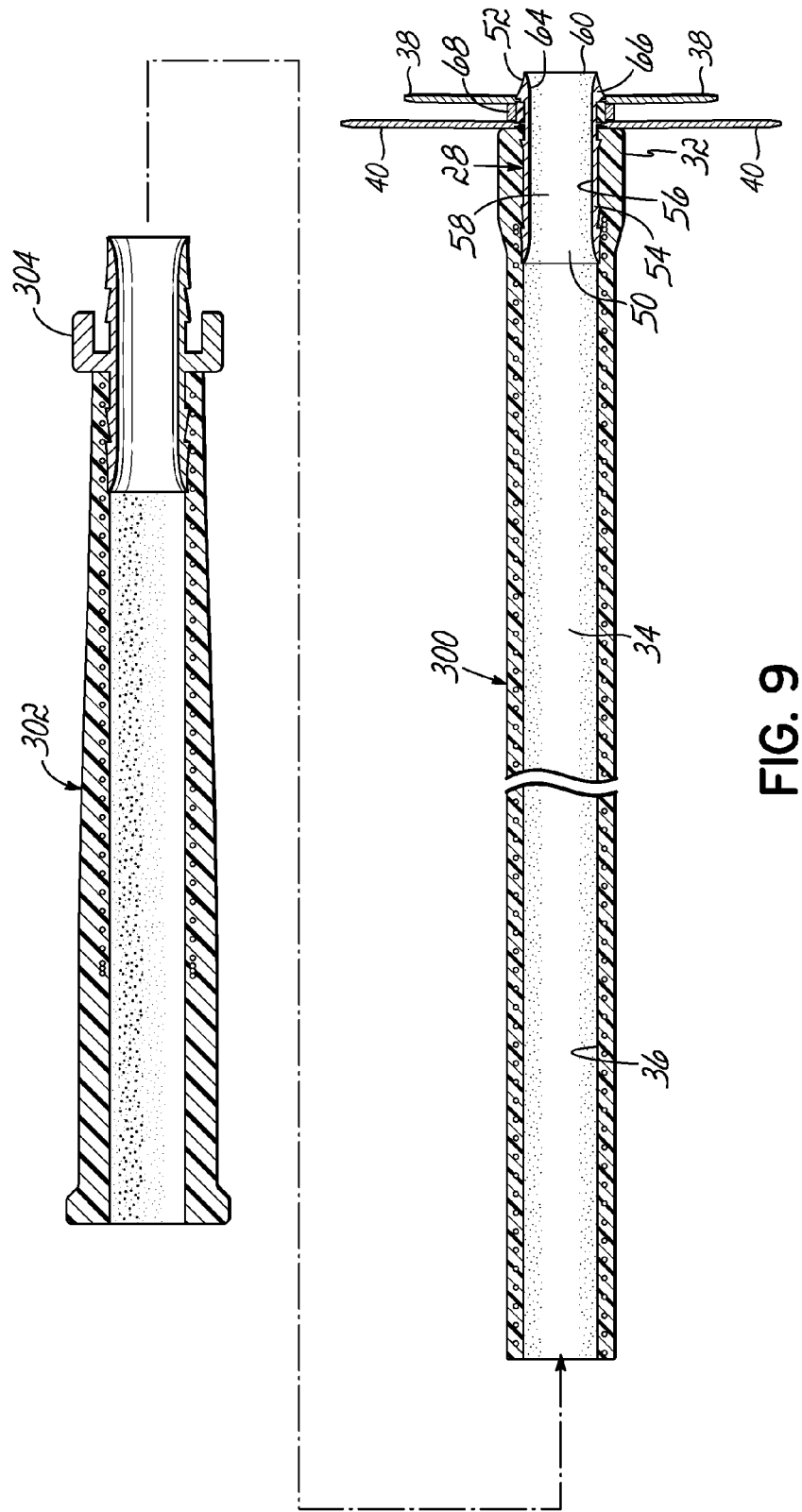
FIG. 9 is a cross-sectional view showing an alternative embodiment of a flexible cannula assembly, a cannula adaptor, and a connector for connecting the flexible cannula assembly and the cannula adaptor.

There is therefore a need to improve the accommodation of patients of different sizes. In order to accommodate for patients of different sizes, In an alternative embodiment, as shown in FIGS. 8 and 9, an alternative embodiment of a cannula set assembly is shown extending from the heart 14 to the inlet port of the pump 16. More particularly, a first cannula assembly 300 extends from the heart 14 to a point outside the heart 14. The second cannula assembly 302 is coupled to the first cannula assembly with a suitable connector 304 and extends therefrom and is coupled to the inlet port of the pump 16. The first cannula assembly includes many features, such as the tip 28, described above with respect to the cannula assembly shown in FIG. 2A. Thus, many of the components of this embodiment are identical or substantially similar to the components described above with reference to the embodiment shown in FIG. 2A, and these components need no additional explanation below. Moreover, the first cannula assembly is directed into the heart 14 in the same manner as described above with respect to the cannula assembly of the first embodiment described in FIG. 2A. Once directed into the heart 14, the distal end, including the tip 28, is coupled to the intra-atrial septum 158 via first and second anchors 38, 40. The proximal end of first cannula assembly extends from the right atrial wall 154. A second cannula assembly, including a proximal portion, a distal portion, and a lumen therebetween is coupled to the first cannula assembly. More particularly, the distal portion of the second cannula assembly is coupled to the proximal portion of the first cannula assembly. The proximal portion of the second cannula assembly is then coupled to the inlet port of pump, which may require the methods and devices according to the teachings of the '580 application discussed herein.

Such a configuration utilizing the first and second cannula assemblies is advantageous in that the first and/or second cannula assemblies may be chosen according to the patient size. Thus, in one embodiment, the surgeon may be presented with a set of cannulae in the operating setting, from which he may be able to choose an outflow cannula, and at least two cannulas that may fluidly communicate the inlet of the pump and the circulatory system (i.e. an artery or a chamber of the heart 14) as just described above. The set of cannulae may include one or more outflow cannulae configured to fluidly communicate the outlet of the pump with the circulatory system, such as an artery. The outflow cannulae may have varying lengths in order to accommodate for varying patient sizes.

The set of cannulae may also include a plurality of first cannula assemblies of varying lengths, or alternatively a single first cannula assembly. In either embodiment, the first cannula assembly includes a proximal portion, a distal portion, and a lumen therebetween. The distal portion may include features that allow the first cannula assembly to be coupled to different structures of the circulatory system. For example, the distal portion may include a tip coupled thereto, such as one of the tips described.

The set of cannulae also includes at least one second cannula assembly, but preferably includes a plurality of second cannula assemblies. Each of the second cannula assemblies includes a proximal portion, a distal portion, and a lumen therebetween. The second cannula assembly acts as a cannula adaptor to connect the proximal portion of the first cannula assembly with the inlet of the pump. Thus, in one embodiment, it is possible to provide at least one outflow cannula, a first cannula assembly, and a plurality of second cannula assemblies of varying lengths. In this embodiment, the surgeon would select one of the second cannula assemblies according to the size of the patient. Thus, the distance also corresponds to the distance between the proximal end of the first cannula and the pump pocket generally. The selection may also be based on a more specific distance from the proximal portion of the first cannula assembly or the inlet of the pump.

In another embodiment, it is possible to provide at least one outflow cannula, a plurality of first cannula assemblies of varying lengths, and a second cannula assembly. In this embodiment, the surgeon would select one of the first cannula assemblies according to the patient size. Because a single second cannula assembly is provided in this embodiment, the length of first cannula assembly will be selected by the surgeon such that the second cannula assembly has a sufficient enough length in order to fluidly communicate the proximal end of the first cannula assembly and the inlet pump. Of course, any distances and/or lengths may be determined or measured directly from the point where the distal portion of the cannula assembly is coupled. Alternatively, the distances and/or lengths may include bends, turns, or other characteristics that must be accounted for. For example, because the cannula assembly may include, in one embodiment, bends and/or curves once implanted, such characteristics may also have to be taken into account when selecting the proper first cannula assembly and/or second cannula assembly.

Figure 10A:
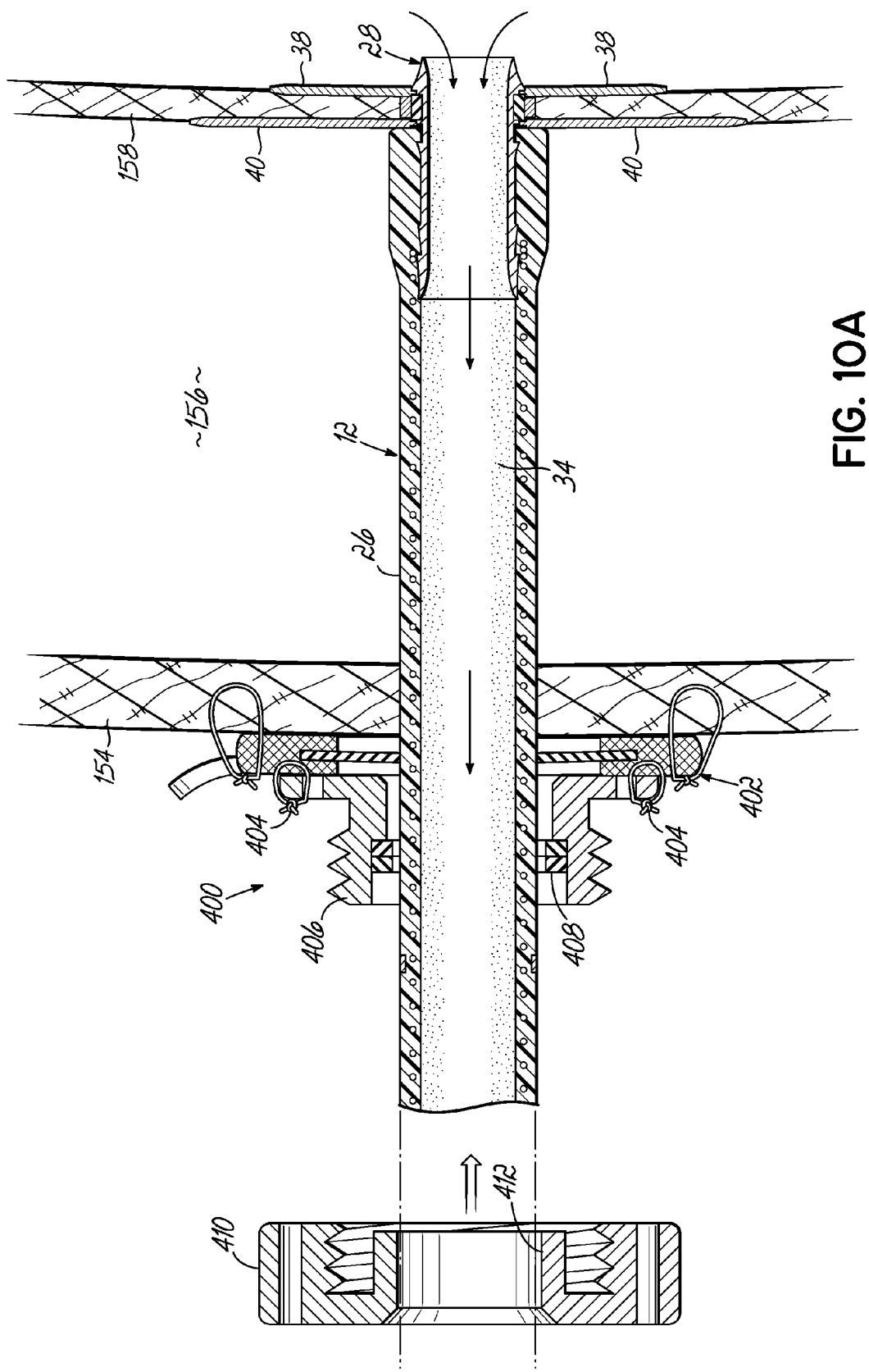
FIG. 10A is a cross sectional view similar to FIG. 4N but showing an alternative embodiment using a coupling for attaching the sewing ring to the heart wall, before assembly.
Figure 10B:
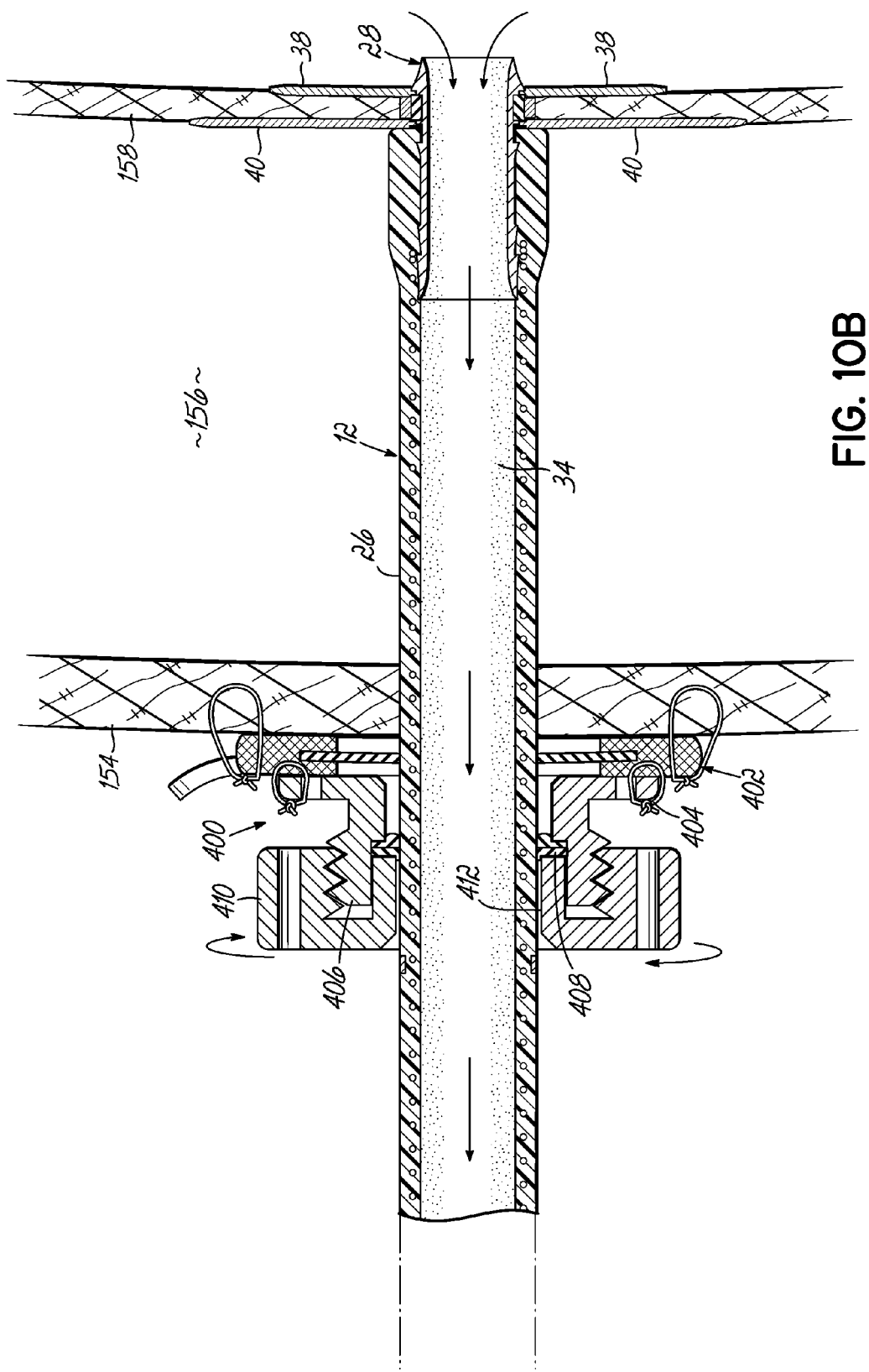
FIG. 10B is a cross sectional view similar to FIG. 10A but showing the coupling in an assembled stated.

FIGS. 10A and 10B illustrate another embodiment. This embodiment may use the same general cannula assembly 12 and other system components previously described, but includes an alternative coupling and sealing structure 400 for securing the cannula assembly 12 to the heart wall 154. In particular, this structure 400 includes a sewing ring structure 402 that is similar to sewing ring structure 184. However, this sewing ring 402 is coupled, such as by using suture 404 to a first externally threaded element 406. The first externally threaded element 406 includes internal elastomeric or otherwise resilient, or flexible sealing structure 408 and is adapted to couple with a second internally threaded element 410 that receives the cannula assembly 12 in an internal through passage 412. As shown in FIG. 10B, the two elements 406, 410 are rotatably coupled together. This compresses the sealing element or elements 408 against the outer surface of the cannula assembly 12 thus creating a fluid tight seal for purposes of hemostasis. Other types of connection structure may be provided instead of threads.

While the present invention has been illustrated by the description of one or more embodiments thereof, and while the embodiments have been described in considerable detail, they are not intended to restrict or in any way limit the scope of the appended claims to such detail. The various features as described herein may be used in the described combinations or in any combination according to the needs of the user. Additional advantages and modifications will readily appear to those skilled in the art. The invention in its broader aspects is therefore not limited to the specific details, representative apparatus and method and illustrative examples shown and described. Accordingly, departures may be from such details without departing from the scope or spirit of the general inventive concept.

What is claimed is:

1. A system for drawing blood from a heart of a patient, comprising:
    a blood pump having an inlet and an outlet;
    an outflow cannula configured to fluidly communicate the outlet to a patient circulatory system;
    a flexible cannula assembly configured to extend through an external wall of the heart, and to an internal structure of the heart to fluidly communicate a chamber of the heart and the inlet, the cannula assembly further comprising:
        a flexible cannula body including a proximal end, a distal end, an inner wall defining a lumen, and an outer wall,
        a tip coupled with the distal end of the cannula body, and
        an anchor coupled to the tip, the anchor configured to engage the internal structure of the heart and operable to resist movement of the cannula assembly in at least one direction along a lengthwise central axis of the flexible cannula body; and
    at least one ring member configured to be coupled to the external wall and positioned at least partially around the outer wall of the cannula body proximally relative to the tip, the at least one ring member further configured to provide hemostasis between the external wall and the cannula body.

2. The system of claim 1, wherein the at least one ring member is further configured to facilitate tissue ingrowth for securing the at least one ring member to the external wall of the heart.

3. The system of claim 1, wherein the at least one ring member defines an aperture sized to interference fit with the outer wall of the cannula body.

4. The system of claim 1, wherein the at least one ring member further comprises:

a radially inner portion defining an aperture sized to interference fit with the outer wall of the cannula body; and a radially outer portion at least partially encapsulating the inner portion and including a porous polymeric structure for facilitating tissue ingrowth.

5. The system of claim 4, wherein the inner portion further comprises a polymeric or rubber-like material.

6. The system of claim 4, wherein at least a portion of the inner layer is positioned axially inward of the outer member.

7. The system of claim 1, wherein the at least one ring member further comprises:

a radially outer edge at least partially surrounding a central axis; and a tab extending radially outward from the outer edge.

8. The system of claim 1, wherein the at least one ring member further comprises:

a first ring member having a first side and a second side, the first ring member configured to be coupled to the external wall such that the first side generally abuts the external wall; and a second ring member configured to be coupled to the second side of the first ring member.

9. The system of claim 8, wherein the second ring member includes a plurality of barbs for engaging the first ring member.

10. The system of claim 1, wherein the at least one ring member is movable relative to the cannula assembly.

11. A method of drawing blood from a heart of a patient using a flexible cannula assembly including a cannula body having a proximal end, a distal end, and a lumen therebetween, and a tip coupled to the distal end of the cannula body, the method comprising:

introducing distal portion of a flexible cannula assembly including a tip through an external wall of the heart such that the tip is in fluid communication with a first chamber of the heart;

advancing the cannula assembly through an internal structure of the heart that separates the first chamber from a second chamber, until the tip is in fluid communication with the second chamber;

deploying an anchor coupled to the tip in order to secure the tip to the internal structure;

coupling a proximal end of the cannula body to an inlet of a pump;

sealing the cannula body to the external wall of the heart to provide hemostasis between the external wall and the cannula body; and operating the pump to draw blood through the tip from the second chamber and into the lumen of the cannula body.

12. The method of claim 11, wherein the external wall is a right atrial wall, a right ventricular wall, or a left atrial wall.

13. The method of claim 11, wherein the internal structure is an intra-atrial septum, an intra-ventricular septum, or a heart valve.

14. The method of claim 11, further comprising:

placing at least one ring member around an outer wall of the cannula body, the at least one ring member defining an aperture sized to interference fit with the outer wall of the cannula body; and coupling the at least one ring member to the external wall of the heart;

wherein the at least one ring member further comprises a first ring member having a first side and a second side, and a second ring member including a plurality of barbs, and the method further comprises:

coupling the first ring member to the external wall such that the first side generally abuts the external wall; and coupling the second ring member to the second side of the first ring member by engaging the barbs with the first ring member.

15. A system for securing a flexible cannula assembly to an external wall and an internal structure of a heart of a patient, comprising:

a flexible cannula assembly, further comprising:

a flexible cannula body including a proximal end, a distal end, an inner wall defining a lumen, and an outer wall, a tip coupled with the distal end of the cannula body, and an anchor coupled to the tip, the anchor configured to engage the internal structure of the heart and operable to resist movement of the cannula assembly in at least one direction along a lengthwise central axis of the flexible cannula body; and at least one ring member configured to be coupled to the external wall and positioned at least partially around the outer wall of the cannula body proximally relative to the tip, the at least one ring member further configured to provide hemostasis between the external wall and the cannula body.

16. A method of securing a flexible cannula assembly to an external wall and an internal structure of a heart of a patient, the flexible cannula assembly including a cannula body having a proximal end, a distal end, and a lumen therebetween, and a tip coupled to the distal end of the cannula body, the method comprising:

introducing distal portion of a flexible cannula assembly including a tip through an external wall of the heart such that the tip is in fluid communication with a first chamber of the heart;

advancing the cannula assembly through an internal structure of the heart that separates the first chamber from a second chamber, until the tip is in fluid communication with the second chamber;

deploying an anchor coupled to the tip in order to secure the tip to the internal structure;

placing at least one ring member around an outer wall of the cannula body, the at least one ring member defining an aperture sized to interference fit with the outer wall of the cannula body; and coupling the at least one ring member to the external wall of the heart to provide hemostasis between the external wall and the cannula body, wherein the at least one ring member is spaced proximally from the tip.

17. A delivery system for delivering a cannula assembly to a heart of a patient, comprising:

a flexible cannula assembly including a cannula body having a proximal portion and a distal portion; and a delivery sheath including a set of rigid jaws movable between an open configuration and a closed configuration, wherein the jaws define a lumen in the closed configuration to receive the cannula assembly for traveling to the heart as a unit with the cannula assembly.

18. The delivery system of claim 17, wherein:

at least a portion of an outer wall of the cannula body includes a first cross-sectional dimension; and at least a portion of the lumen of the delivery sheath includes a second cross-sectional dimension smaller than the first cross-sectional dimension such that the jaws must be in the open configuration to move the delivery sheath relative to the cannula assembly in at least one direction.

19. The delivery system of claim 18, wherein a proximal portion of the outer wall of the cannula body includes the first cross-sectional dimension and a distal portion of the outer wall of the cannula body includes a third cross-sectional dimension smaller than the second cross-sectional dimension, such that the lumen is configured to receive at least the distal portion of the cannula body for traveling to the heart as a unit with the cannula assembly.

20. The delivery system of claim 17, wherein:
in the closed position, each of the jaws extends substantially parallel to a central axis of the lumen.

21. The delivery system of claim 17, wherein:
the lumen is essentially circular in cross section.

22. The delivery system of claim 17, wherein the delivery sheath further comprises:
a proximal portion and a distal portion, the lumen extending between the proximal portion and the distal portion; and
a seal element at the proximal portion of the delivery sheath configured to seal at least the proximal portion when the delivery sheath receives at least a portion of the cannula assembly.

23. The delivery system of claim 22, wherein the seal element defines an aperture when the jaws are in the closed configuration.

24. The delivery system of claim 23, wherein the aperture is sized to be in an interference fit with an outer cross-sectional dimension of the cannula body such that the seal member provides hemostasis between the delivery sheath and the cannula body when the delivery sheath receives at least a portion of the cannula assembly.

25. The delivery system of claim 22, wherein the seal element includes a first portion coupled to one of the jaws and a second portion coupled to the other of the jaws.

26. The delivery system of claim 22, wherein the seal element further comprises a lubricious element configured to reduce the frictional force between the seal element and the cannula body as the cannula assembly moves relative to the delivery sheath.

27. The delivery system of claim 17, wherein the delivery sheath further comprises:
a set of handle members hingedly coupled to one another, each of the handle members coupled to one of the jaws and being operable to move the jaws relative to one another and between the open configuration and closed configuration.

28. The delivery system of claim 27, further comprising:
a locking mechanism operably coupled to at least one of the jaws or at least one of the handle members, the locking mechanism having a first locking state and a second locking state;
wherein the jaws are permitted to move relative to one another when the locking mechanism is in the first locking state and prevented from moving relative to one another when the locking mechanism is in the second locking state.

29. The delivery system of claim 27, wherein:
the jaws extend along an axis; and
at least a portion of each of the handle members is positioned at an angle relative to the axis.

30. The delivery system of claim 17, further comprising:
a balloon catheter adapted to expand and engage the delivery sheath to enable the delivery sheath to traverse an external wall or an internal structure of the heart.

31. The delivery system of claim 30, wherein the balloon catheter is adapted to expand and engage the cannula assembly to allow relative movement between the cannula assembly and the delivery sheath.

32. The delivery system of claim 17, further comprising:
a stop member coupled to at least one of the cannula assembly or the delivery sheath, the stop member configured to allow a predetermined amount of movement of the cannula assembly relative to the delivery sheath.

33. The delivery system of claim 32, wherein:
the stop member is removably coupled to the cannula assembly.

34. A method of implanting a circulatory assist system for assisting in the flow of blood through a patient circulatory system, the circulatory assist system comprising a flexible cannula assembly for directing blood from the heart of a patient, the cannula assembly comprising a cannula body including a proximal end, a distal portion, and a lumen therebetween, the method comprising:
directing a guide-element through an external wall of the heart;
further directing the guide-element into the heart such that a distal portion of the guide element is positioned adjacent to an internal structure of the heart;
inserting a delivery system over the guide-element, through the external wall and adjacent the internal structure, wherein the delivery system includes the cannula assembly and a delivery sheath having a set of rigid jaws movable between an open configuration and a closed configuration, wherein the jaws define a lumen in the closed configuration to receive the cannula assembly for movement relative thereto;
moving the cannula assembly relative to the delivery sheath such that at least a distal portion of the cannula extends distally from the delivery sheath;
coupling the distal portion of the cannula assembly to the internal structure;
retracting the delivery sheath towards a proximal portion of the cannula assembly and back through the external wall; and
moving the jaws to the open configuration and further retracting the delivery sheath.

35. The method of claim 34, further comprising:
moving the jaws from the open configuration to the closed configuration; and
loading the cannula assembly into the lumen of the delivery sheath.

36. The method of claim 34, wherein the cannula assembly further comprises a tip coupled with the distal portion of the cannula assembly, and at least a first anchor coupled to the tip, the first anchor configured to be deployed from a contracted state to an expanded state, wherein the first anchor is configured to engage the internal structure of the heart in the expanded state, and coupling the distal portion of the cannula assembly to the internal structure further comprises:
moving the cannula assembly relative to the delivery sheath so as to deploy the first anchor from the contracted state into the expanded state, thereby engaging the internal structure.

37. The method of claim 36, wherein the cannula assembly further comprises a second anchor coupled to the tip and configured to be deployed from a contracted state to an expanded state, wherein the second anchor is configured to engage an opposite side of the internal structure in the expanded state as the first anchor; and the method further comprises:

moving the delivery sheath relative to the cannula assembly so as to deploy the second anchor from the contracted state into the expanded state, thereby engaging the internal structure.

38. The method of claim 36, wherein the delivery system further comprises a stop member coupled to at least one of the cannula assembly or the delivery sheath, and moving the cannula assembly relative to the delivery sheath so as to deploy the first anchor further comprises:

moving the cannula assembly relative to the delivery sheath a predetermined distance until the stop member prevents further movement of the cannula assembly relative to the delivery sheath.

39. The method of 38, further comprising:

decoupling the stop member from the cannula assembly and/or the delivery sheath, before retracting the delivery sheath towards the proximal portion of the cannula assembly.

40. The method of claim 34, further comprising:

directing a distal end of a piercing device through the external wall of the heart; and advancing the distal end of the piercing device adjacent to the internal structure of the heart;

wherein directing the directing a guide-element through the external wall of the heart and further directing the guide-element adjacent to the internal structure of the heart includes directing the guide element through a lumen of the piercing device.

41. The method of claim 34, wherein the external wall is a right atrial wall and the internal structure is an intra-atrial septum.

42. The method of claim 34, further comprising:

creating an incision substantially near an intercostal space and directing the guide-element from the incision through the intercostal space and to the heart.

43. The method of claim 42, wherein the intercostal space is a fourth intercostal space, fifth intercostal space, or sixth intercostal space.

44. The method of claim 43, further comprising:

further retracting the delivery sheath and removing the delivery sheath through the incision.

45. The method of claim 34, wherein the delivery sheath further comprises a set of handle members operable to move the jaws relative to one another and between the open and closed configurations, and a locking mechanism operably coupled to at least one of the jaws or at least one of the handle members configured to selectively permit or prevent movement of the jaws, and the opening the jaws further comprises:

unlocking the locking mechanism.

46. The method of claim 34, wherein at least a portion of an outer wall of the cannula body includes a first cross-sectional dimension, and the lumen of the delivery sheath includes a second cross-sectional dimension smaller than the first cross-sectional dimension, and the method further comprises:

moving the delivery sheath in the closed configuration in a proximal direction relative to the cannula assembly until reaching the portion of the cannula body having the first cross-sectional dimension; and moving the jaws to the open configuration once a proximal portion of the jaws contacts or approaches the portion of the cannula body having the first cross-sectional dimension so as to allow further proximal movement of the delivery sheath relative to the cannula assembly.

47. The method of claim 34, wherein the cannula assembly further comprises a tip coupled to the distal portion of the cannula assembly, and first and second anchors coupled to the tip, each of the first and second anchors being configured to be deployed from a contracted state to an expanded state, wherein the first and second anchors are configured to engage opposite sides of a heart tissue in the expanded state, and the method further comprises:

directing the cannula assembly into a first end of the delivery sheath in the closed configuration such that the first and second anchors are folded in a first direction to the contracted state;

moving at least the distal portion of the cannula assembly out of the first end or a second opposing end of the delivery sheath such that one of the first or second anchors exits from the first end or second end of the delivery sheath and deploys into the expanded state; and moving the distal portion back towards the first end or the second end of the delivery sheath such that the expanded first or second anchor folds in a second direction opposite of the first direction and into the contracted state.

48. The method of claim 34, wherein inserting the delivery system further comprises:

coupling a first ring member to the external wall of the heart, the ring defining an aperture;

directing the delivery system through the aperture and through the external wall; and pulling the first ring member in a direction generally away from the heart as the delivery system is directed through the aperture and through the external wall.

49. The method of claim 48, wherein coupling the ring member further comprises:

sewing the first ring member to the external wall of the heart.

50. The method of claim 48, wherein the first ring member includes an outer edge at least partially circumscribing a central axis, and a tab extending from the outer edge, and pulling the first ring member further comprises:

pulling the tab in the direction generally away from the heart.

\* \* \* \* \*